United States Patent [19]
Chambers et al.

[11] Patent Number: 5,929,082
[45] Date of Patent: Jul. 27, 1999

[54] POTASSIUM ION CHANNEL BLOCKERS

[75] Inventors: Noel John Chambers, Cres Ballina; Graham Allen Ross Johnston, Roseville, both of Australia

[73] Assignees: Polychip Pharmaceuticals Pty Ltd, Toorak; The University of Sydney, Sydney, both of Australia

[21] Appl. No.: 08/913,769

[22] PCT Filed: Mar. 21, 1996

[86] PCT No.: PCT/AU96/00151

§ 371 Date: Jan. 23, 1998

§ 102(e) Date: Jan. 23, 1998

[87] PCT Pub. No.: WO96/30341

PCT Pub. Date: Oct. 3, 1996

[30]  Foreign Application Priority Data

Mar. 24, 1995 [AU] Australia ................. PN-1930

[51] Int. Cl.$^6$ ............. C07D 213/75; C07D 239/47; A61K 31/44; A61K 31/505
[52] U.S. Cl. ............. 514/272; 514/353; 544/318; 546/306
[58] Field of Search ............. 544/318; 546/306; 514/353, 272

[56]  References Cited

FOREIGN PATENT DOCUMENTS

| 72742/81 | 7/1981 | Australia . |
| 467 709 A2 | 1/1992 | European Pat. Off. . |
| 3234451 | 3/1984 | Germany . |
| WO 83/00627 | 3/1983 | WIPO . |
| 94/10086 | 5/1993 | WIPO . |
| WO 94/04499 | 3/1994 | WIPO . |
| WO 94/04500 | 3/1994 | WIPO . |

OTHER PUBLICATIONS

J. Med. Chem. 1990, vol. 33, No. 9, pp. 2393–2407; "Novel Agents Effective against . . . ", Howbert, et al.

Chemical Abstracts, vol. 106, No. 13, Mar. 30, 1987, Abstract No. 95588.

*Primary Examiner*—Zinna Northington Davis
*Attorney, Agent, or Firm*—Larson & Taylor

[57]  ABSTRACT

The invention provides novel sulphonylurea, sulphonylthiourea and sulphonylguanidine compounds which have the ability to block potassium ion channels regulated by intracellular concentrations of ATP. Methods of synthesis, pharmaceutical compositions and methods for the treatment of conditions such as type II diabetes, cardiac arrhythmias, ischaemic and hypoxic cardiovascular incidents, and cancers are also claimed.

15 Claims, 5 Drawing Sheets

POTASSIUM ION CHANNEL BLOCKERS

This application is a 371 of PCT/AU96/00151 filed Mar. 21, 1996.

This invention relates to compounds which have the ability to block potassium ion channels. In particular, the invention relates to sulphonylurea, sulphonylthiourea and sulphonylguanidine compounds which act to block potassium ion channels regulated by intracellular concentrations of adenosine triphosphate (ATP). The compounds of the invention are therefore useful in the treatment of conditions such as type II diabetes, cardiac arrhythmias, and ischaemic and hypoxic cardiovascular incidents.

BACKGROUND OF THE INVENTION

Potassium ion channels are responsible for the control and maintenance of many physiological responses, and a wide variety of such channels is known The many classes and subclasses of potassium ion channels allow for the development of new chemical entities which specifically allow or impede the passage of potassium ions ($K^+$) through these channels, thus altering the physiological state of the cell. Compounds which have the ability to modulate the passage of $K^+$ through a subset of potassium ion channels which is regulated by the concentration of adenosine triphosphate (ATP) are known as $K_{ATP}$ channel blockers or $K_{ATP}$ openers, depending on whether they impede or enhance the passage of $K^+$.

Alteration of potassium ion channel flux causes variations in the excitable state of a number of tissues; open potassium channels allow the membrane potential to come closer to the potassium equilibrium potential, so that the membrane potential is more stable and less likely to fire (Cook, 1990). Potassium ion channels are also associated with the resting potential, and periods of excitability are terminated by these channels. Thus, by modulating the $K^+$ ion movement through these channels, the ensuing responses may be of therapeutic benefit.

Type II diabetes is an example of a disease that is effectively treated with, potassium ion channel blockers of the sulphonylurea type with relative safety. Such drugs include tolbutamide and glyburide. Ideally these drugs display both rapid onset and short duration of action, thus reducing the risk of chronic hyperinsulinaemia, which is a risk factor for atherosclerosis, and of potentially fatal hypoglycaemic incidents Thus discontinuous exposure appears to be best during long term treatment, because the plasma drug concentration falls below the threshold level during at least part of the night, since desensitisation appears to be associated with the use of high concentrations of and continuous exposure to sulphonylureas (Palmer and Brogden, 1993).

The $K_{ATP}$ blockers alter the regulation of insulin secretion from pancreatic β cells. This effect results from the fact that the $K_{ATP}$ channels which maintain the cell membrane resting potential are generally open in resting conditions, but close due to an increase in intracellular ATP following glucose metabolism Depolarisation of the β cell membrane occurs upon closure of these channels. This induces the activation of the voltage-dependent calcium channels, promoting an influx of $Ca^{2+}$ into the cells, which facilitates the secretion of insulin from β cells (Gopalakrishnan et al, 1993). These compounds have also been demonstrated to have the ability to alter $K^+$ channel flux in a variety of non-pancreatic tissues by blocking ATP dependent channels, and may be beneficial for the treatment of other diseases (Robertson and Steinberg, 1990).

The possibilities for therapeutic effects on the heart are numerous, as during diastole the myocardium exhibits a stable high resting membrane potential which is maintained predominantly by $K^+$ channel currents These currents also regulate the termination of excitation in the myocardium and pacemaker tissue (Cook, 1990). Thus many conditions requiring both emergency care and post-emergency care have the potential to be ameliorated by agents modulating the relevant $K^+$ channel currents associated with the particular problem Furthermore, under abnormal conditions other parts of the heart, particularly the A-V node and Purkinje fibres, exhibit self excitation, and thus display an intrinsic rhythmic rate of their own which contrasts to the normal rate of contraction. Thus by stabilising the resting membrane potential in these tissues it is possible that these arrhythmias may be controlled Blockers of the ATP-dependent $K^+$ channels may prevent or reduce ischaemia-induced ventricular arrhythmias by preventing loss of $K^+$ through these channels, as demonstrated by the effect of glibenclamide (1 $\mu M$) when tested in rat heart stimulated at 5 Hz (Kantor et al, 1987).

Potassium ion channel modulators have demonstrated the ability to induce physiological changes in many tissues The effects of these modulators in the pancreas and the heart have been outlined above, with specific reference to the $K_{ATP}$ channel blockers In addition, some $K_{ATP}$ channel openers, such as the non-specific $K^+$ opener pinacidil, have been found to have vasodilator activity, and are useful as anti-hypersensitive agents (Cohen, 1986).

Neuronal $K_{ATP}$ channels have also demonstrated an association with transmitter release. The neurotransmitter γ-aminobutyric acid (GABA) is released from the substantia nigra, and this release is mediated via $K_{ATP}$ channels. $K_{ATP}$ channel closure induced by sulphonylurea compounds elicits an increase in intracellular $Ca^{2+}$ analogous to that described in the pancreas, resulting in the stimulation of GABA secretion (Schmid-Antomarchi et al, 1990).

The potential for the use of $K_{ATP}$ channel blockers as anti-cancer agents has recently been highlighted with the finding that in cultured MCF-7 human mammary carcinoma cells, reversible cell-cycle arrest arises from the inhibition of $K_{ATP}$ channels following treatment with $K_{ATP}$ channel blockers such as Glibenclamide. Cells exposed to Glibenclamide exhibited a concentration-dependent inhibition of cell proliferation, with an IC50 value of 50 $\mu M$. Cell populations exposed to Glibenclamide also exhibited a statistically significant accumulation at the G0/G1 phase in cell cycle distribution. (Woodfork et al, 1995).

We have now found a novel family of sulphonyl compounds which have potassium ion channel blocking activity, and which are useful in the treatment of conditions mediated by potassium ion movement through these channels. Such conditions include, but are not limited to, type II diabetes, cardiac arrhythmias ischaemic and hypoxic cardiovascular incidents, and cancers.

SUMMARY OF THE INVENTION

According to one aspect of the present invention there is provided a sulphonyl compound of general formulae selected from the group consisting of formulae I, II, III, IV and V:

where
R represents a substituted or unsubstituted alkylaryl, benzyl or alkyl group;
X represents oxygen, sulphur, amine, or guanidine;
W represents nitrogen or carbon; and
Y, Q and Z independently represent hydrogen, halogen, amine, alkyl, hydroxy, alkoxy, sulphonylurea, sulphonylthiourea or sulphonylguandine, where each of Y, Q and Z may be the same or different,
with the proviso that in formula I, when X is O, Y and Z are not both hydrogen, and in formula IV, X is not O, Y and Z are not $CH_3$, Q is not H, and R is not $C_6H_4CH_3$.

By "alkylaryl" is meant a group having a single 6-membered aromatic ring.

The ring moiety of the alkylaryl group or the benzyl group may be substituted with groups such as chlorine, bromine, ethyl, or methoxy.

The alkyl moiety of the alkylaryl group may be straight or branched, and it is also preferably hydrophobic; it may be of substantial chain length, for example up to 20 carbons.

By "alkyl" is meant a straight or branched, saturated or unsaturated, substituted or unsubstituted alkyl chain, which may again be long, for example up to 20 carbons. Preferably the chain is saturated. Where the chain is substituted, the substituent groups are preferably hydrophobic.

A very wide variety of alkyl or alkylaryl substituents, including long chain substituents, has been used in known sulphonylurea, sulphonylthiourea and sulphonylguanidine groups, and similar groups are suitable for use in the present invention.

By "alkoxyl" is meant a substituted or unsubstituted alkoxy group of 1 to 6 carbon atoms, preferably 1 to 3 carbon atoms. The alkyl moiety may be substituted or unsaturated, and may be straight or branched.

Where X is amino or guanidine, or Y, Q or Z is amine, these may optionally be substituted.

The halogen is preferably chlorine, bromine or iodine, and more preferably is bromine.

In general formulae I to IV, Y, Q or Z as appropriate may be sulphonylurea, and where this is the case, the sulphonylurea group is preferably symmetrical with the sulphonylurea chain which is substituted by the R group.

Preferred compounds of the invention are those of the general formulae I to V as defined above wherein
R represents an alkylaryl group;
X represents oxygen or sulphur;
W represents nitrogen or carbon; and
Y, Q and Z independently represent hydrogen, halogen, amino, alkyl, hydroxy, sulphonylurea or alkoxy, where each of Y, Q and Z may be the same or different.

In a particularly preferred embodiment, the compound of the invention is of general formula I, II or III, and the pyridine ring is substituted by an ethoxy group.

Prior art studies on sulphonylurea, sulphonylthiourea and sulphonylguanidine compounds have concentrated on varying the R group. Compounds in which the urea or guanidine chain is linked to a pyridine group have received relatively little attention. R groups of the types used in the prior art are suitable for use in the present invention.

Some preliminary evidence suggests that certain metabolites of compounds according to the invention may also have the ability to block potassium ion channels, and it will be clearly understood that metabolites having this biological activity fall within the scope of the invention Such compounds are referred to herein as "active metabolites".

According to a second aspect of the present invention there is provided a process for the preparation of compounds of the general formulae I, II, III, IV and V as defined above which comprises the step of reacting a compound of the general formulae VI, VII, VIII or IX respectively:

wherein W, Y, Z, and Q are as defined above, with a compound of the general formula X:

wherein X and R again are as defined above.

The reaction of the heterocyclic amines of the general formulae VI to IX with the isocyanate or isothiocyanate of general formula X may be carried out in any suitable solvent, such as tetrahydrofuran or toluene. The reaction is typically conducted between room temperature and 100° C. in the absence or presence of base.

Reactants used in the preparation of compounds of the present are largely known in the chemical literature.

According to a third aspect, the invention provides a pharmaceutical composition comprising a compound of formula selected from general formulae I, II, III, IV and V as defined above, together with a pharmaceutically-acceptable carrier.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., U.S.A.

According to a fourth aspect, the invention provides a method of treatment of a condition mediated by alteration of potassium ion channel flux, comprising the step of administering an effective amount of a compound of formula selected from the group consisting of general formulae I, II, III, IV and V, or an active metabolite thereof, to a mammal in need of such treatment.

Preferably the condition mediated by potassium ion channel flux is selected from the group consisting of type II diabetes, cardiac arrhythmias, and ischaemic and hypoxic cardiovascular incidents.

DETAILED DESCRIPTION OF THE INVENTION

The invention will now be described with reference to the following non-limiting examples.

Representative examples of compounds of the invention are given in Tables 1 to 5 below.

The compound of Example 1, 4,6-dimethyl-2-pyrimidyl-N-[4-methylphenyl)sulphonyl]-N'-urea, is known, and is specifically excluded from the scope of the invention. It is referred to herein for purposes of comparison only.

TABLE 1

I

| Compound | X | Y | Z | R |
|---|---|---|---|---|
| 1-1 | O | Br— | H | —$C_6H_4CH_3$ |
| 1-2 | O | HO— | H | —$C_6H_4CH_3$ |
| 1-3 | O | $CH_3O$— | H | —$C_6H_4CH_3$ |
| 1-4 | O | $CH_3CH_2O$— | H | —$C_6H_4CH_3$ |
| 1-5 | O | $CH_3CH_2CH_2O$— | H | —$C_6H_4CH_3$ |
| 1-6 | O | $CH_3CH_2OOC$— | H | —$C_6H_4CH_3$ |
| 1-7 | O | $H_2N$— | H | —$C_6H_4CH_3$ |
| 1-8 | O | H | Br— | —$C_6H_4CH_3$ |
| 1-9 | O | H | HO— | —$C_6H_4CH_3$ |
| 1-10 | O | H | $CH_3O$— | —$C_6H_4CH_3$ |
| 1-11 | O | H | $CH_3CH_2O$— | —$C_6H_4CH_3$ |
| 1-12 | O | H | $CH_3CH_2CH_2O$— | —$C_6H_4CH_3$ |
| 1-13 | O | H | $CH_3CH_2OOC$— | —$C_6H_4CH_3$ |
| 1-14 | O | H | $H_2N$— | —$C_6H_4CH_3$ |
| 1-15 | O | $CH_3CH_2O$— | $CH_3CH_2O$— | —$C_6H_4CH_3$ |
| 1-16 | O | $CH_3CH_2OOC$— | $CH_3CH_2OOC$— | —$C_6H_4CH_3$ |
| 1-17 | O | $RSO_2NHCONH$— | H | —$C_6H_4CH_3$ |
| 1-18 | O | H | $RSO_2NHCONH$— | —$C_6H_4CH_3$ |
| 1-19 | O | $CH_3CH_2O$— | H | —$CH_2(CH_3)_3$ |
| 1-20 | O | H | $CH_3CH_2O$— | —$CH_2(CH_3)_3$ |
| 1-21 | S | Br— | H | —$C_6H_4CH_3$ |
| 1-22 | S | HO— | H | —$C_6H_4CH_3$ |
| 1-23 | S | $CH_3O$— | H | —$C_6H_4CH_3$ |
| 1-24 | S | $CH_3CH_2O$— | H | —$C_6H_4CH_3$ |
| 1-25 | S | $CH_3CH_2CH_2O$— | H | —$C_6H_4CH_3$ |
| 1-26 | S | $CH_3CH_2OOC$— | H | —$C_6H_4CH_3$ |
| 1-27 | S | $H_2N$— | H | —$C_6H_4CH_3$ |
| 1-28 | S | H | Br— | —$C_6H_4CH_3$ |
| 1-29 | S | H | HO— | —$C_6H_4CH_3$ |
| 1-30 | S | H | $CH_3O$— | —$C_6H_4CH_3$ |
| 1-31 | S | H | $CH_3CH_2O$— | —$C_6H_4CH_3$ |
| 1-32 | S | H | $CH_3CH_2CH_2O$— | —$C_6H_4CH_3$ |
| 1-33 | S | H | $CH_3CH_2OOC$— | —$C_6H_4CH_3$ |
| 1-34 | S | H | $H_2N$— | —$C_6H_4CH_3$ |
| 1-35 | S | $CH_3CH_2O$— | $CH_3CH_2O$— | —$C_6H_4CH_3$ |
| 1-36 | S | $CH_3CH_2OOC$— | $CH_3CH_2OOC$— | —$C_6H_4CH_3$ |
| 1-37 | S | $RSO_2NHCSNH$— | H | —$C_6H_4CH_3$ |
| 1-38 | S | H | $RSO_2NHCSNH$— | —$C_6H_4CH_3$ |
| 1-39 | S | $RSO_2NHCSNH$— | $RSO_2NHCSNH$— | —$C_6H_4CH_3$ |
| 1-40 | S | $CH_3CH_2O$— | H | —$CH_2(CH_3)_3$ |
| 1-41 | S | H | $CH_3CH_2O$— | —$CH_2(CH_3)_3$ |
| 1-42 | S | H | H | —$CH_2(CH_3)_3$ |

TABLE 2

II

| Compound | X | Y | Z | R |
|---|---|---|---|---|
| 2-1 | O | Br— | H | —$C_6H_4CH_3$ |
| 2-2 | O | HO— | H | —$C_6H_4CH_3$ |
| 2-3 | O | $CH_3O$— | H | —$C_6H_4CH_3$ |
| 2-4 | O | $CH_3CH_2O$— | H | —$C_6H_4CH_3$ |
| 2-5 | O | $CH_3CH_2CH_2O$— | H | —$C_6H_4CH_3$ |
| 2-6 | O | $CH_3CH_2OOC$— | H | —$C_6H_4CH_3$ |

TABLE 2-continued

II

Y-[pyridine with Z]-NH-C(X)-NH-SO2-R

| Compound | X | Y | Z | R |
|---|---|---|---|---|
| 2-7 | O | H₂N— | H | —C₆H₄CH₃ |
| 2-8 | O | H | Br— | —C₆H₄CH₃ |
| 2-9 | O | H | HO— | —C₆H₄CH₃ |
| 2-10 | O | H | CH₃O— | —C₆H₄CH₃ |
| 2-11 | O | H | CH₃CH₂O— | —C₆H₄CH₃ |
| 2-12 | O | H | CH₃CH₂CH₂O— | —C₆H₄CH₃ |
| 2-13 | O | H | CH₃CH₂OOC— | —C₆H₄CH₃ |
| 2-14 | O | H | H₂N— | —C₆H₄CH₃ |
| 2-15 | O | CH₃CH₂O— | CH₃CH₂O— | —C₆H₄CH₃ |
| 2-16 | O | CH₃CH₂OOC— | CH₃CH₂OOC— | —C₆H₄CH₃ |
| 2-17 | O | RSO₂NHCONH— | H | —C₆H₄CH₃ |
| 2-18 | O | H | RSO₂NHCONH— | —C₆H₄CH₃ |
| 2-19 | O | CH₃CH₂O— | H | —CH₂(CH₃)₃ |
| 2-20 | O | H | CH₃CH₂O— | —CH₂(CH₃)₃ |
| 2-21 | S | Br— | H | —C₆H₄CH₃ |
| 2-22 | S | HO— | H | —C₆H₄CH₃ |
| 2-23 | S | CH₃O— | H | —C₆H₄CH₃ |
| 2-24 | S | CH₃CH₂O— | H | —C₆H₄CH₃ |
| 2-25 | S | CH₃CH₂CH₂O— | H | —C₆H₄CH₃ |
| 2-26 | S | CH₃CH₂OOC— | H | —C₆H₄CH₃ |
| 2-27 | S | H₂N— | H | —C₆H₄CH₃ |
| 2-28 | S | H | Br— | —C₆H₄CH₃ |
| 2-29 | S | H | HO— | —C₆H₄CH₃ |
| 2-30 | S | H | CH₃O— | —C₆H₄CH₃ |
| 2-31 | S | H | CH₃CH₂O— | —C₆H₄CH₃ |
| 2-32 | S | H | CH₃CH₂CH₂O— | —C₆H₄CH₃ |
| 2-33 | S | H | CH₃CH₂OOC— | —C₆H₄CH₃ |
| 2-34 | S | H | H₂N— | —C₆H₄CH₃ |
| 2-35 | S | CH₃CH₂O— | CH₃CH₂O— | —C₆H₄CH₃ |
| 2-36 | S | CH₃CH₂OOC— | CH₃CH₂OOC— | —C₆H₄CH₃ |
| 2-37 | S | RSO₂NHCSNH— | H | —C₆H₄CH₃ |
| 2-38 | S | H | RSO₂NHCSNH— | —C₆H₄CH₃ |
| 2-39 | S | CH₃CH₂O— | H | —CH₂(CH₃)₃ |
| 2-40 | S | H | CH₃CH₂O— | —CH₂(CH₃)₃ |
| 2-41 | S | H | H | —CH₂(CH₃)₃ |

TABLE 3

III

| Compound | X | Y | Z | R |
|---|---|---|---|---|
| 3-1 | O | Br— | H | —C₆H₄CH₃ |
| 3-2 | O | HO— | H | —C₆H₄CH₃ |
| 3-3 | O | CH₃O— | H | —C₆H₄CH₃ |
| 3-4 | O | CH₃CH₂O— | H | —C₆H₄CH₃ |
| 3-5 | O | CH₃CH₂CH₂O— | H | —C₆H₄CH₃ |
| 3-6 | O | CH₃CH₂OOC— | H | —C₆H₄CH₃ |
| 3-7 | O | H₂N— | H | —C₆H₄CH₃ |
| 3-8 | O | CH₃CH₂O— | CH₃CH₂O— | —C₆H₄CH₃ |
| 3-9 | O | CH₃CH₂OOC— | CH₃CH₂OOC— | —C₆H₄CH₃ |
| 3-10 | O | RSO₂NHCONH— | H | —C₆H₄CH₃ |
| 3-11 | O | CH₃CH₂O— | H | —CH₂(CH₃)₃ |
| 3-12 | S | Br— | H | —C₆H₄CH₃ |
| 3-13 | S | HO— | H | —C₆H₄CH₃ |
| 3-14 | S | CH₃O— | H | —C₆H₄CH₃ |
| 3-15 | S | CH₃CH₂O— | H | —C₆H₄CH₃ |
| 3-16 | S | CH₃CH₂CH₂O— | H | —C₆H₄CH₃ |
| 3-17 | S | CH₃CH₂OOC— | H | —C₆H₄CH₃ |
| 3-18 | S | H₂N— | H | —C₆H₄CH₃ |
| 3-19 | S | CH₃CH₂O— | CH₃CH₂O— | —C₆H₄CH₃ |
| 3-20 | S | CH₃CH₂OOC— | CH₃CH₂OOC— | —C₆H₄CH₃ |
| 3-21 | S | RSO₂NHCSNH— | H | —C₆H₄CH₃ |
| 3-22 | S | CH₃CH₂O— | H | —CH₂(CH₃)₃ |
| 3-23 | S | H | H | —CH₂(CH₃)₃ |
| 3-24 | S | Br | Br | —C₆H₄CH₃ |

TABLE 4

IV

| Compound | X | Y | Q | Z | R |
|---|---|---|---|---|---|
| 4-1 | O | Br— | H | H | —C₆H₄CH₃ |
| 4-2 | O | HO— | H | H | —C₆H₄CH₃ |
| 4-3 | O | CH₃O— | H | H | —C₆H₄CH₃ |
| 4-4 | O | CH₃CH₂O— | H | H | —C₆H₄CH₃ |
| 4-5 | O | CH₃CH₂CH₂O— | H | H | —C₆H₄CH₃ |
| 4-6 | O | CH₃CH₂OOC— | H | H | —C₆H₄CH₃ |
| 4-7 | O | H₂N— | H | H | —C₆H₄CH₃ |
| 4-8 | O | H | Br— | H | —C₆H₄CH₃ |

TABLE 4-continued

IV

| Compound | X | Y | Q | Z | R |
|---|---|---|---|---|---|
| 4-9 | O | H | HO— | H | —C$_6$H$_4$CH$_3$ |
| 4-10 | O | H | CH$_3$O— | H | —C$_6$H$_4$CH$_3$ |
| 4-11 | O | H | CH$_3$CH$_2$O— | H | —C$_6$H$_4$CH$_3$ |
| 4-12 | O | H | CH$_3$CH$_2$CH$_2$O— | H | —C$_6$H$_4$CH$_3$ |
| 4-13 | O | H | CH$_3$CH$_2$OOC— | H | —C$_6$H$_4$CH$_3$ |
| 4-14 | O | H | H$_2$N— | H | —C$_6$H$_4$CH$_3$ |
| 4-15 | O | HOOC— | HOOC— | H | —C$_6$H$_4$CH$_3$ |
| 4-16 | O | CH$_3$CH$_2$OOC— | CH$_3$CH$_2$OOC— | H | —C$_6$H$_4$CH$_3$ |
| 4-17 | O | CH$_3$CH$_2$OOC— | H | CH$_3$CH$_2$OOC— | —C$_6$H$_4$CH$_3$ |
| 4-18 | O | RSO$_2$NHCONH— | H | H | —C$_6$H$_4$CH$_3$ |
| 4-19 | O | CH$_3$CH$_2$O— | H | CH$_3$CH$_2$O— | —CH$_2$(CH$_3$)$_3$ |
| 4-20 | O | CH$_3$CH$_2$O— | H | H | —CH$_2$(CH$_3$)$_3$ |
| 4-21 | O | H | CH$_3$CH$_2$O— | H | —CH$_2$(CH$_3$)$_3$ |
| 4-22 | S | Br— | H | H | —C$_6$H$_4$CH$_3$ |
| 4-23 | S | HO— | H | H | —C$_6$H$_4$CH$_3$ |
| 4-24 | S | CH$_3$O— | H | H | —C$_6$H$_4$CH$_3$ |
| 4-25 | S | CH$_3$CH$_2$O— | H | H | —C$_6$H$_4$CH$_3$ |
| 4-26 | S | CH$_3$CH$_2$CH$_2$O— | H | H | —C$_6$H$_4$CH$_3$ |
| 4-27 | S | CH$_3$CH$_2$OOC— | H | H | —C$_6$H$_4$CH$_3$ |
| 4-28 | S | H$_2$N— | H | H | —C$_6$H$_4$CH$_3$ |
| 4-29 | S | H | Br— | H | —C$_6$H$_4$CH$_3$ |
| 4-30 | S | H | HO— | H | —C$_6$H$_4$CH$_3$ |
| 4-31 | S | H | CH$_3$O— | H | —C$_6$H$_4$CH$_3$ |
| 4-32 | S | H | CH$_3$CH$_2$O— | H | —C$_6$H$_4$CH$_3$ |
| 4-33 | S | H | CH$_3$CH$_2$CH$_2$O— | H | —C$_6$H$_4$CH$_3$ |
| 4-34 | S | H | CH$_3$CH$_2$OOC— | H | —C$_6$H$_4$CH$_3$ |
| 4-35 | S | H | H$_2$N— | H | —C$_6$H$_4$CH$_3$ |
| 4-36 | S | CH$_3$— | H | CH$_3$— | —C$_6$H$_4$CH$_3$ |
| 4-37 | S | CH$_3$CH$_2$O— | H | CH$_3$CH$_2$O— | —C$_6$H$_4$CH$_3$ |
| 4-38 | S | CH$_3$CH$_2$OOC— | CH$_3$CH$_2$OOC— | H | —C$_6$H$_4$CH$_3$ |
| 4-39 | S | RSO$_2$NHCSNH— | H | H | —C$_6$H$_4$CH$_3$ |
| 4-40 | S | CH$_3$CH$_2$O— | H | CH$_3$CH$_2$O— | —CH$_2$(CH$_3$)$_3$ |
| 4-41 | S | CH$_3$CH$_2$O— | H | H | —CH$_2$(CH$_3$)$_3$ |
| 4-42 | S | H | CH$_3$CH$_2$O— | H | —CH$_2$(CH$_3$)$_3$ |

TABLE 5

V

| Compound | W | Y | Q | Z | R |
|---|---|---|---|---|---|
| 5-1 | C | Br— | H | H | —C$_6$H$_4$CH$_3$ |
| 5-2 | C | HO— | H | H | —C$_6$H$_4$CH$_3$ |
| 5-3 | C | CH$_3$O— | H | H | —C$_6$H$_4$CH$_3$ |
| 5-4 | C | CH$_3$CH$_2$O— | H | H | —C$_6$H$_4$CH$_3$ |
| 5-5 | C | CH$_3$CH$_2$CH$_2$O— | H | H | —C$_6$H$_4$CH$_3$ |

TABLE 5-continued

V

[Structure: pyrimidine ring with substituents Y, Q, Z, W, and bis-sulfonylurea group R—S(O)₂—NH—C(=N-pyrimidyl)—NH—S(O)₂—R]

| Compound | W | Y | Q | Z | R |
|---|---|---|---|---|---|
| 5-6 | C | CH₃CH₂OOC— | H | H | —C₆H₄CH₃ |
| 5-7 | C | H₂N— | H | H | —C₆H₄CH₃ |
| 5-8 | C | H | Br— | H | —C₆H₄CH₃ |
| 5-9 | C | H | HO— | H | —C₆H₄CH₃ |
| 5-10 | C | H | CH₃O— | H | —C₆H₄CH₃ |
| 5-11 | C | H | CH₃CH₂O— | H | —C₆H₄CH₃ |
| 5-12 | C | H | CH₃CH₂CH₂O— | H | —C₆H₄CH₃ |
| 5-13 | C | H | CH₃CH₂OOC— | H | —C₆H₄CH₃ |
| 5-14 | C | H | H₂N— | H | —C₆H₄CH₃ |
| 5-15 | C | CH₃CH₂O— | H | CH₃CH₂O— | —C₆H₄CH₃ |
| 5-16 | C | CH₃CH₂OOC— | H | CH₃CH₂OOC— | —C₆H₄CH₃ |
| 5-17 | C | CH₃CH₂OOC— | CH₃CH₂OOC— | H | —C₆H₄CH₃ |
| 5-18 | C | CH₃— | CH₃— | H | —C₆H₄CH₃ |
| 5-19 | C | RSO₂NHCONH— | H | H | —C₆H₄CH₃ |
| 5-20 | C | CH₃CH₂O— | H | CH₃CH₂O— | —CH₂(CH₃)₃ |
| 5-21 | C | CH₃CH₂O— | H | H | —CH₂(CH₃)₃ |
| 5-22 | C | H | CH₃CH₂O— | H | —CH₂(CH₃)₃ |
| 5-23 | N | Br— | H | H | —C₆H₄CH₃ |
| 5-24 | N | HO— | H | H | —C₆H₄CH₃ |
| 5-25 | N | CH₃O— | H | H | —C₆H₄CH₃ |
| 5-26 | N | CH₃CH₂O— | H | H | —C₆H₄CH₃ |
| 5-27 | N | CH₃CH₂CH₂O— | H | H | —C₆H₄CH₃ |
| 5-28 | N | CH₃CH₂OOC— | H | H | —C₆H₄CH₃ |
| 5-29 | N | H₂N— | H | H | —C₆H₄CH₃ |
| 5-30 | N | H | Br— | H | —C₆H₄CH₃ |
| 5-31 | N | H | HO— | H | —C₆H₄CH₃ |
| 5-32 | N | H | CH₃O— | H | —C₆H₄CH₃ |
| 5-33 | N | H | CH₃CH₂O— | H | —C₆H₄CH₃ |
| 5-34 | N | H | CH₃CH₂CH₂O— | H | —C₆H₄CH₃ |
| 5-35 | N | H | CH₃CH₂OOC— | H | —C₆H₄CH₃ |
| 5-36 | N | H | H₂N— | H | —C₆H₄CH₃ |
| 5-37 | N | CH₃CH₂O— | H | CH₃CH₂O— | —C₆H₄CH₃ |
| 5-38 | N | CH₃CH₂OOC— | H | CH₃CH₂OOC— | —C₆H₄CH₃ |
| 5-39 | N | CH₃CH₂OOC— | CH₃CH₂OOC— | H | —C₆H₄CH₃ |
| 5-40 | N | CH₃— | CH₃— | H | —C₆H₄CH₃ |
| 5-41 | N | RSO₂NHCONH— | H | H | —C₆H₄CH₃ |
| 5-42 | N | CH₃— | H | CH₃— | —C₆H₄CH₃ |
| 5-43 | N | CH₃CH₂O— | H | CH₃CH₂O— | —CH₂(CH₃)₃ |
| 5-44 | N | CH₃CH₂O— | H | H | —CH₂(CH₃)₃ |
| 5-45 | N | H | CH₃CH₂O— | H | —CH₂(CH₃)₃ |

Example 1 4,6-dimethyl-2-pyrimidyl-N-[4-methylphenyl) sulphonyl]-N'-urea

As stated above, this compound is known, and its synthesis is included as a comparative example.

2-Amino-4,6-dimethylpyrimidine (200 mg, 1.6 mmol) was stirred in toluene (4 ml) under a nitrogen atmosphere. p-Toluenesulphonylisocyanate (0.3 ml, 460 mg, 2.3 mmol) was added and stirring continued for 4 hours at room temperature. The mixture was then filtered and the precipitate washed with toluene and chloroform to give white 4,6-dimethyl-2-pyrimidyl-N-[4-methylphenyl)sulphonyl]-N'-urea (500 mg, 96% yield), m.p. 205–207° C., lit. m.p. 221° C. dec. $v_{max}$ (KBr disc) 3158w, 1698s, 1605s, 1556m, 1449s, 1350s, 1165s, 1087m, 875w, 814w, 681w, 558s cm⁻¹.

¹H n.m.r. spectrum (300 MHz) δ 2.45, s, 3xCH₃; 6.75, 1H'; 7.31–8.00, AA'BB', 4H (H3, H5 and H2, H6 respectively); 8.83, brs, NH. Mass spectrum: m/z 321 (H+1, 100%), 256 (3), 150 (4), 124 (16).

Example 2 N-[(4-Methylphenyl)sulphonyl]-N'-(6-ethoxypyrid-2-yl)urea (Compound 1-4)

2-Amino-6-ethoxypyridine (17 g, 12.7 mmol) was stirred in toluene (20 ml) at room temperature under a nitrogen atmosphere. N-(4-methylphenyl)sulphonylisothiocyanate (1.7 ml, 2.6 g, 13.2 mmol) was added slowly, and stirring continued for 2 hours. The precipitate was then removed by filtration, dissolved in sodium hydroxide and then acidified with hydrochloric acid until precipitation. Filtration gave N-[(4-methylphenyl)sulphonyl]-N'-(6-ethoxypyrid-2-yl)

urea (3.59 g, 85%) as a white powder, m.p. 197–199° C. (Found: C, 54.1; H, 5.1; N, 12.1; O, 19.3; S, 9.2. $C_{15}H_{17}N_3O_4S$ requires C, 53.7; H, 5.1; N, 12.5; O, 19.1; S, 9.6%). $v_{max}$ (KBr disc) 3230w, 3083w, 2981m, 1702s, 1580s, 1454m, 1432s, 1352m, 1246m, 1168s, 1093m, 797m, 687m, 539m cm$^{-1}$. $^1$H n.m.r. spectrum (300 MHz): δ 1.45, t, $J_{CH3}$, 7 Hz, $CH_3$; 2.43, s, CH3; 4.33, q, $J_{CH2}$, 7 Hz, $CH_2$; 6.36–7.51, m, 3H'; 7.31–7.97, AA'BB', 4H (H3, H5 and H2, H6 respectively). Mass spectrum: m/z 336 (M+1, 100%), 244 (1), 201 (100), 212 (3), 198 (25), 172 (33), 139 (89).

Example 3 4,5-Diethyl-2-pyrimidyl-N-[4-methylphenyl) sulphonyl)-N'-urea dicarboxylate (Compound 4-16)

2-Amino-4,5-diethylpyrimidine dicarboxylate (400 mg, 1.67 mmol) was stirred in toluene (8 ml) under a nitrogen atmosphere. p-Toluenesulphonylisocyanate (0.3 ml, 460 mg, 2.3 mmol) was added and stirring continued overnight at room temperature. The mixture was then filtered and the precipitate washed with toluene and recrystallised from chloroform to give white 4,5-diethyl-2-pyrimidyl-N-[4-methylphenyl)sulphonyl]-N'-urea dicarboxylate (630 mg, 86%), m.p. 163–164° C. (Found: C, 49.6; H, 4.6; N, 12.8; O, 25.8; S, 6.8. $C_{18}H_{20}N_4O_7S$ requires C, 49.5; H, 4.6; N, 12.8; O, 25.7; S, 7.3%). $v_{max}$ (KBr disc) 3221m, 3139m, 2291m, 1734s, 1696s, 1586s, 1470s, 1438s, 1358s, 1297s, 1162s, 1087m, 1022m, 891m, 813m, 709m, 696w, 547m cm$^{-1}$. $^1$H n.m.r. spectrum (300 MHz): δ 1.36–1.45, m, $2CH_3$; 2.44, s, $CH_3$, 4.40, q, $CH_2$, $J_{CH2}$, 10.7 Hz; 4.47, q, CH2, JCH2, 10.7 Hz 7.31–8.00, AA'BB', 4H (H3, H5 and H2, H6 respectively); 9.12, s, H4. Mass spectrum: m/z 436 (H+1, 100%), 240 (63), 198 (69).

Example 4 N-[(4-Methylphenyl)sulphonyl-N'-(6-ethoxypyrid-2-yl)thiourea (Compound 1-24)

N-(4-methylphenyl)sulphonylisothiocyanate (1.75 g, 8.2 mmol) was dissolved in toluene (25 ml) at room temperature. 2-Amino-6-ethoxypyridine (1.1 g, 8.2 mmol) was added, and the mixture refluxed overnight. Upon cooling the precipitate was removed by filtration, washed with toluene and dichloromethane, then air dried. Washing with warm methanol gave N-[(4-methylphenyl)sulphonyl]-N,-(6-ethoxypyrid-2-yl)thiourea (1.12 g, 43%), m.p. 196–197° C. (Found: C, 51.6; H, 4.7; N, 12.0%. $C_{15}H_{17}N_3O_3S_2$ requires C, 51.3; H, 4.9; N, 12.0%). $v_{max}$ (KBr disc) 3188w, 3026w, 2984w, 1704w, 1632m, 1538s, 1432s, 1352s, 1218s, 1170s, 1090m, 950w, 789m, 655m, 523m cm$^{-1}$. $^1$H n.m.r. spectrum (300 MHz): δ 1.49, t, $J_{CH3}$, 7.05 Hz, $CH_3$, 2.44, s, $CH_3$; 4.41, q, $J_{CH2}$, 7.14 Hz, $CH_2$; 6.46–7.59, m, 3H'; 7.31–7.96, AA'BB', 4H (H3, H5 and H2, H6 respectively). Mass spectrum: m/z 351 (H+1, 13%), 336 (8), 318 (5), 238 (5), 226 (14), 214 (27), 198 (65), 181 (25), 172 (31), 157 (41), 139 (100), 125 (30), 111 (19).

Example 5 N-[(4-Methylphenyl)sulphonyl]-N'-(4,6-dimethylypyrimid-2-yl)thiourea (Compound 4-36)

2- Amino-4,6-dimethylpyrimidine (1 g, 8.13 mmol) and N-(4-methylphenyl)sulphonylisothiocyanate (2 g, 9.39 mmol) were refluxed overnight in toluene (30 ml). Upon cooling the precipitate was removed by filtration, then washed with toluene giving N-[(4-methylphenyl) sulphonyl]-N'-(4,6-dimethylpyrimid-2-yl)thiourea (2.08 g, 76.1%) as opaque crystals, m.p. 160–161° C. dec. (note a crystal structure change at 131° C.). (Found: C, 50.4; H, 5.0; N, 16.7. $C_{14}H_{16}N_4O_2S_2$ requires C, 50.0; H, 4.8; N, 16.7%). vmax (KBr disc) 3470w, 3308w, 3159w, 3013w, 2867w, 1613m, 1524s, 1486m, 1430m, 1352m, 1184m, 1164s, 1088w, 931w, 814w, 654w, 562m cm$^{-1}$. $^1$H n.m.r. spectrum (300 MHz): δ NH; 1.63, s, 1H'; 2.31, s, $CH_3$; 2.44, s, $2xCH_3$; 6.40, sbr, NH; 6.79, s, H'; 7.31–8.01, AA'BB', 4H (H3, H5 and H2, H6 respectively); 8.61, sbr, NH. Mass spectrum: m/z 337 (M+1, 68%), 305 (3), 271 (6), 229 (15), 211 (25), 183 (93), 166 (39), 157 (43), 149 (37), 139 (18), 124 (100).

Example 6 N,N'-Di-[4-methylphenyl)sulphonyl]-N"(4,5-diethyl-2-pyrimidyl-dicarboxylate)guanidine (Compound 5-39)

N-(4-Methylphenyl)sulphonylisothiocyanate (0.93 g, 4.4 mmol) was dissolved at room temperature in toluene (20 ml). Diethyl-2-amino-4,5-pyrimidinedicarboxylate (0.93 g, 3.9 mmol) was then added and the mixture stirred at room temperature for one hour. Diisopropylethylamine (10 drops) was then added and stirring continued overnight. The precipitate was removed by filtration, washed with toluene and recrystallised from ethanol and water to give N,N'-Di-[4-methylphenyl)sulphonyl]-N"(4,5-diethyl-2-pyrimidyl-dicarboxylate)guanidine (670 mg, 29%), m.p. 205–206° C. (Found: C, 51.2; H, 4.5; N, 11.6. $C_{25}H_{27}N_5O_8S_2$ requires C, 50.9; H, 4.6; N, 11.9%). vmax (KBr disc) 3160w, 3076w, 2987w, 1748m, 1716m, 1627s, 1555s, 1473m, 1361s, 1302s, 1173m, 1066w, 917w, 813m, 693m, 546m cm$^{-1}$. $^1$H n.m.r. spectrum (300 MHz): δ 1.37–1.47, m, $2xCH_3$; 2.41, s, $CH_3$; 2.44, s, $CH_3$; 4.42, q, $CH_2$, $J_{CH2}$, 10.7 Hz; 4.50, q, $CH_2$, $J_{CH2}$, 10.7 Hz; 7.20–7.77, AA'BB', 4H (H3, H5 and H2, H6 respectively); 7.26–7.90, AA'BB', 4H" (H3", H5" and H2", H6" respectively); 9.17, s, H4; 10.79, brs, NH. Mass spectrum: m/z 590 (H+1, 99%), 526 (9), 454 (19), 436 (100), 391 (9), 371 (15), 282 (12), 257 (10), 240 (40), 225 (13), 197 (15), 171 (30), 157 (75), 139 (53), 125 (80).

Example 7 4-Amino-3-pyridyl-N-[4-methylphenyl) sulphonyl]-N'-urea (Compound 2-14)

3,4-Diaminopyridine (0.5 g, 4.7 mmol) was stirred at 60° C. in toluene (20 ml) under a nitrogen atmosphere. p-Toluenesulphonylisocyanate (0.6 ml, 0.92 g, 4.7 mmol) was added and stirring continued for 3 days at 60° C. The mixture was then allowed to cool to room temperature. The mixture was then filtered and the precipitate washed with toluene and then recrystallised from water to give 4-amino-3-pyridyl-N-[4-methylphenyl)sulphonyl]-N'-urea (515 mg, 36%), m.p. 150–152° C. $v_{max}$ (KBr disc) 3447m, 3394m, 3343m, 3209s, 3144s, 3009m, 1666s, 1595s, 1567s, 1422s, 1253s, 1158s, 1057s, 827s, 670s, 534s cm$^{-1}$. $^1$H n.m.r. spectrum (300 MHz): δ 2.36, s, $CH_3$; 7.01, brs, $NH_2$; 6.70–7.72, m, 3H'; 7.14–7.73, AA'BB', 4H (H3, H5 and H2, H6 respectively); 7.61, s, NH. Mass spectrum: m/z 304 (M-2, 59%), 281 (10), 256 (10), 171 (47), 155 (30), 109 (100), 91 (43), 81 (14), 55 (37).

Example 8 N-[(4-Methylphenyl)sulphonyl]-N'-(6-aminopyrid-2-yl)urea (Compound 1-7)

2,6-Diaminopyridine (200 mg, 1.8 mmol) and N-(4-methylphenyl)sulphonylisocyanate (0.24 ml 0.37 g, 1 equiv) were stirred in toluene (10 ml) under a nitrogen atmosphere at approximately 0° C. for 3 hours. The white gelatinous mixture was filtered, washed with toluene and chloroform, then allowed to dry in a dessicator. The white solid was dissolved in base, filtered, then reacidified and the precipitate collected. The precipitate was then stirred in hot chloroform, cooled, and filtered. The insoluble solid was then washed with ethylacetate and recrystallised from methanol to give N-[(4-methylphenyl)sulphonyl]-N'-(6-aminopyrid-2-yl)urea as fine opaque needles (410 mg, 73%), m.p. 155–157° C. (Found. C, 48.5, H, 5.2; N, 17.6 $C_{13}H_{14}N_4.O_3S. H_2O$ requires C, 48.1, H, 5.0; N, 17.3%). $v_{max}$ (KBr disc) 3553w, 3412w, 3271m, 3157m, 2914w, 1657s, 1598s, 1550m, 1449w, 1391m, 1342m, 1245s, 1138s, 1089m, 1054m, 888m, 779w, 541m cm$^{-1}$. $^1$H n.m.r. spectrum (300 MHz): δ b 2.41, s, $CH_3$; 3.07, brs, $NH_2$;

7.41–7.46, m, 3H'; 7.23–7.89, AA'BB', 4H (H3, H5 and H2, H6 respectively). Mass spectrum: m/z 307 (H+1, 63%), 198 (82), 172 (100), 155 (27), 136 (32), 110 (71).

Example 9 N-((4-Methylphenyl)sulphonyl]-N'-(6-bromopyrid-2-yl)urea (Compound 1-1)

2-Amino-6-bromopyridine (1.0 g, 5.3 mmol) was stirred in toluene (20 ml) at room temperature under a nitrogen atmosphere. N-(4-methylphenyl)sulphonylisothiocyanate (0.75 ml, 1.15 g, 5.8 mmol) was added slowly, and stirring continued for 2 hours. The precipitate was then removed by filtration, dissolved in sodium hydroxide and then acidified with hydrochloric acid until precipitation which was collected by filtration. Recrystallisation from ethanol gave N-[(4-methylphenyl)sulphonyl]-N -(6-bromopyrid-2-yl) urea (1.77 g, 83%) as a white powder, m.p. >310° C. (Found: C, 42.3, H, 3.3; N, 11.2. $C_{13}H_{12}N_3O_3SBr$ requires C, 42.2; H, 3.3; N, 11.4%) $v_{max}$ (KBr disc) 3436m, 3404m, 1630s, 1561s, 1509s, 1385s, 1271s, 1223s, 1137s, 1066s, 869m, 789m, 665m, 554s cm$^{-1}$. $^1$H n.m.r. spectrum (300 MHz): δ 2.43, s, CH$_3$; 2.58, sbr, 2×NH; 7.09–7.47, m, 3H', 4H' and 5H'; m, 3H; 7.32–7.96, AA'BB', 4H (H3, H5 and H2, H6 respectively) Mass spectrum: m/z 371 (H+1, 1%), 218 (18), 201 (100), 199 (99), 173 (97), 137 (10), 121 (53).

Example 10 2-Pyrimidyl-N-[4-methylphenyl) sulphonyl]-N'-urea-4,5-dicarboxylic acid (Compound 4-15)

4,5-Diethyl-2-pyrimidyl-N-[4-methylphenyl)sulphonyl]-N'-urea dicarboxylate (200 mg, 0.46 mmol) was dissolved in sodium hydroxide (1M ,15 ml) and heated with stirring for 1 hour. The solution was allowed to cool, then acidified with hydrochloric acid (6M), the precipitate collected by filtration and washed with water then chloroform. Drying gave white 2-pyrimidyl-N-[4-methylphenyl)sulphonyl]-N'-urea-4,5-dicarboxylic acid (112 mg, 65%), m.p. 194–196° C. (Found: C, 40.4; H, 3.6; N, 13.1. $C_{14}H_{12}N_4O_7S.2H_2O$ requires C, 40.4; H, 3.4; N, 13.5%) $v_{max}$ (KBr disc) 3410brm, 3130brm, 1726s, 1687s, 1583s, 1470s, 1344s, 1235m, 1164s, 1086m, 961w, 818m, 710m, 546m cm$^{-1}$. $^1$H n.m.r. spectrum (300 MHz): δ 2.44, s, CH$_3$; 3.40, sbr, NH; 7.31–7.99, AA'BB', 4H (H3, H5 and H2, H6 respectively); 9.13, s, H6'; 10.37, brs, NH; 12.02, brs, NH. Mass spectrum: 212 (4), 198 (5), 189 (9), 183 (2), 172 (100), 155 (8), 135 (7).

Example 11 N-((4-Methylphenyl)sulphonyl)]-N'-(3-pyridyl)thiourea (Compound 2-41)

N-(4-Methylphenyl)sulphonylisothiocyanate (200 mg, 0.94 mmol) and 4-aminopyridine (90 mg, 1.0 mmol) was stirred in toluene (10 ml) for 30 minutes, potassium hydroxide was added and stirring continued for a further hour. The mixture was then refluxed at 120° C. for 5 hours then allowed to cool. The precipitate was removed by filtration, dissolved in water and acidified with dilute hydrochloric acid. N-[(4-Methylphenyl)sulphonyl)]-N'-(3-pyridyl) thiourea (221 mg, 72%) was then air dried (m.p.129–132° C.). $v_{max}$ (KBr disc) 3357m, 3259m, 3051w, 2633w, 1597w, 1558w, 1495w, 1389w, 1302m, 1155s, 1096w, 904w, 818m, 704w, 534m cm$^{-1}$. $^1$H n.m.r. spectrum (300 MHz): δ 2.41, s, CH$_3$; 6.93, sbr, NH; 7.26–7.79, m, 3H'; 7.27–7.79, AA'BB', 4H (H3, H5 and H2, H6 respectively) Mass spectrum: m/z 308 (H+1, 75%), 292 (27), 214 (97), 200 (10), 172 (100), 155 (91), 135 (7), 123 (24).

Example 12 N-[(4-Methylphenyl)sulphonyl]-N'-(2-pyridyl)thiourea (Compound 1-42)

2-Aminopyridine (0.9 g, 9.6 mmol) and N-(4-methylphenyl)sulphonylisothiocyanate (2 g, 9.4 mmol) were refluxed overnight in toluene (35 ml). Upon cooling the precipitate was removed by filtration, then washed with toluene giving N-[(4-methylphenyl)sulphonyl]-N'-(2-pyridyl)thiourea (1.4 g, 49.3%) as a white powder, m.p. 154–155° C. dec. (Found: C, 49.5, H, 4.5; N, 13.3. $C_{13}H_{13}N_3O_2S_2.\frac{1}{2}H_2O$ requires C, 49.4; H, 4.5, N, 13.3%) $v_{max}$ (KBr disc) 3482w, 3268w, 3029brw, 1640m, 1606s, 1559m, 1474m, 1388m, 1340m, 1149s, 1087m, 959w, 727m, 656m, 523m cm$^{-1}$. $^1$H n.m.r. spectrum (300 MHz): δ 2.43, s, CH$_3$, 7.04–8.29, m, 4H'; 7.30–7.98, AA'BB', 4H (H3, H5 and H2, H6 respectively). Mass spectrum: m/z 308 (H+1, 66%), 274 (5), 242 (7), 214 (100), 172 (10), 165 (13), 155 (65), 135 (37), 123 (96).

Example 13 N-[(4-Methylphenyl)sulphonyl]-N'-(4-pyridyl)thiourea (Compound 3-23)

4-Aminopyridine (250 mg, 266 mmol) and N-(4-methylphenyl)sulphonylisothiocyanate (500 mg, 235 mmol) were stirred in tetrahydrofuran (20 ml) for 2 hours at room temperature. The yellow precipitate was then removed by filtration and washed with tetrahydrofuran leaving small opaque plates of N-[(4-methylphenyl)sulphonyl]-N'-(4-pyridyl)thiourea (390 mg, 54%) m.p. 124–125° C. dec. (Found: C, 50.5; H, 4.5; N, 13.9. $C_{13}H_{13}N_3O_2S_2$ requires C, 50.8; H, 4.3; N, 13.7%). $v_{max}$ (KBr disc) 3304m, 3203m, 2055m, 1644s, 1599m, 1530s, 1445s, 1326m, 1278s, 1145s, 1077s, 979s, 812s, 540s cm$^{-1}$. $^1$H n.m.r. spectrum (300 MHz): δ 2.39, s, CH$_3$; 6.71–9.33, m, 4H'; 7.24–7.94, AA'BB', 4H (H3, H5 and H2, H6 respectively). Mass spectrum: m/z 306 (H-1, 2%), 260 (9), 246 (36), 214 (73), 198 (11), 172 (29), 155 (18), 135 (53), 123 (100).

Example 14 N-[(4-Methylphenyl)sulphonyl]-N'-(6-bromopyrid-2-yl)thiourea (Compound 1-21)

2-Amino-6-bromopyridine (0.9 g, 5.2 mmol) and N-(4-methylphenyl)sulphonylisothiocyanate (1.1 g, 5.16 mmol) were refluxed overnight in toluene (35 ml). Upon cooling the precipitate was removed by filtration, then washed with toluene and dichloromethane giving N-[(4-methylphenyl) sulphonyl]-N'-(6-bromopyrid-2-yl)thiourea (1.1 g, 55.2%) as opaque crystals, m.p. 175–176° C. dec. (Found: C, 40.5; H, 3.1; N, 10.6. $C_{13}H_{12}N_3O_2S_2Br$ requires C, 40.4; H, 3.1; N, 10.9%). $v_{max}$ (KBr disc) 3270w, 3076w, 3000w, 2860w, 1592m, 1517m, 1439m, 1347m, 1196m, 1159s, 1090w, 952w, 793w, 658w, 544m cm$^{-1}$. $^1$H n.m.r. spectrum (300 MHz): δ 2.44, s, CH$_3$; 7.20–7.57, m, 3H'; 7.32–7.99, AA'BB', 4H (H3, H5 and H2, H6 respectively). Mass spectrum: m/z 388 (H+2, 13%), 386 (M, 13%), 232 (6), 214 (27), 201 (11), 175 (95), 173 (100), 155 (18), 135 (9), 125 (15).

Example 15 N-[(4-Methylphenyl)sulphonyl]-N'-(4-aminopyrid-3-yl)thiourea (Compound 2-34)

3,4-Diaminopyridine (0.19 g, 1.74 mmol) was refluxed with N-(4-methylphenyl)sulphonylisothiocyanate (0.3 g, 1.8 mmol) in toluene (10 ml) overnight. The precipitate was then removed by filtration and washed thoroughly with cold dichloromethane, to give N-[(4-methylphenyl)sulphonyl]-N'-(4-aminopyrid-3-yl)thiourea (200 mg, 37.6%), m.p. 185–187° C. $v_{max}$ (KBr disc) 3418w, 3291m, 3152s, 3030m, 2947m, 1654s, 1565m, 1488s, 1337s, 1241w, 1155s, 1090m, 971w, 816w, 747w, 660w, 545w cm$^{-1}$. $^1$H n.m.r. spectrum (300 MHz): δ 2.45, s, CH$_3$; 7.00–7.81, m, 3H'; 7.33–7.94, AA'BB', 4H (H3, H5 and H2, H6 respectively); 8.34, sbr, NH2. Mass spectrum: m/z 323 (H+1, 5%), 289 (13), 231 (5), 214 (55), 200 (17), 189 (23), 172 (79), 152 (54), 138 (43), 125 (14), 111 (100).

Example 16 N-[(4-Methylphenyl)sulphonyl]-N'-(6-aminopyrid-2-yl)thiourea (Compound 2-27)

2,6-Diaminopyridine (0.5 g, 4.58 mmol) and N-(4-methylphenyl)sulphonylisothiocyanate (1 g, 469 mmol) were stirred in tetrahydrofuran (20 ml) for 5 days at room temperature. The precipitate was then removed by filtration, and dissolved in dilute sodium hydroxide (3M). Upon acidification with dilute hydrochloric acid (3M) the mixture was allowed to stand at 5° C. overnight. The precipitate was then collected by filtration giving fine pale yellow needles of N-[(4-methylphenyl)sulphonyl]-N'-(6-aminopyrid-2-yl) thiourea (1.45 g, 89.5%), m.p. 136–138° C. dec. (Found: C, 44.5; H, 4.5; N, 15.9. $C_{13}H_{14}N_4O_2S_2.1.5\ H_2O$ requires C, 44.7; H, 4.9; N, 16.0%). $v_{max}$ (KBr disc) 3412m, 3150m, 2993w, 1659m, 1604s, 1491w, 1407m, 1273m, 1152s, 1088m, 996w, 729m, 604w, 532w $cm^{-1}$. $^1H$ n.m.r. spectrum (300 MHz): δ 2.42, s, $CH_3$; 5.15, sbr, NH; 6.22–7.42, m, 3H'; 7.29–7.98, AA'BB', 4H (H3, H5 and H2, H6 respectively); 10.33, sbr, NH. Mass spectrum: m/z 323 (M+1, 13%), 214 (69), 200 (17), 172 (3), 155 (25), 138 (16), 125 (3), 110 (100).

Example 17 N,N'-Di-[(4-methylphenyl)sulphonyl]-N"-(2,6-pyridyl)thiourea (Compound 1-39)

N-(4-Methylphenyl)sulphonylisocyanate (2.0 g 9.4 mmol) was dissolved in toluene (35 ml) at room temperature. To the stirring mixture was added 2,6-Diaminopyridine (1 g, 8.1 mmol) and the solution refluxed overnight. Upon cooling the precipitate was removed by filtration, washed with toluene and recrystallised from ethanol and water to give N,N'-di-[(4-methylphenyl)sulphonyl]-N"-(2,6-pyridyl) thiourea (887 mg, 21%), m.p. 186–188° C. $v_{max}$ (KBr disc) 3346m, 3217w, 3100w, 2995w, 1657s, 1630s, 1526m, 1464s, 1401s, 1307m, 1275s, 1141s, 1078s, 840m, 765m, 673m, 551m $cm^{-1}$. $^1H$ n.m.r. spectrum (300 MHz): δ 2.39, s, $CH_3$; 2.41, s, $CH_3$; 5.82, s, NH, 5.85, s, NH; 6.38–7.31, m, 3H'; 7.22–7.88,2×AA'BB', 2×4H (H3, H5 and H2, H6 respectively) 8.19, sbr, NH; 8.22, sbr, NH. Mass spectrum: m/z 534 (M−1, <0.1%), 411 (7), 371 (12), 257 (11), 229 (6), 172 (3), 153 (6), 135 (15), 110 (100).

Example 18 N,N'-Di-[(4-methylphenyl)sulphonyl]-N"-(4,6-dimethylpyrimid-2-yl)guanidine (Compound 5-40)

N-[(4-Methylphenyl)sulphonyl]-N'-(4,6-dimethylpyrimid-2-yl)thiourea (1.1 g, 3.4 mmol) and 1,3-dicyclohexylcarbodiimide (12 g, 4.6 mmol) were stirred at room temperature in acetonitrile (10 ml). To this stirring mixture was added cyanamide (0.3 g, 7 mmol) and a catalytic amount of diisopropylethylamine (5 drops), and the mixture allowed to stir at room temperature for 3 days. The solvent was then removed under vacuum, sodium hydroxide (1M, 10 ml) added with stirring and any solid removed by filtration. The aqueous phase was then acidified with hydrochloric acid (1M), and the precipitate collected by filtration. Recrystallisation from methanol gave N,N'-di-[(4-methylphenyl)sulphonyl]-N"-(4,6-dimethylpyrimid-2-yl) guanidine (157 mg, 10%), m.p. 171–172° C. dec. $v_{max}$ (KBr disc) 3267w, 3232w, 3065w, 2925w, 1634s, 1618s, 1610s, 1541s, 1492m, 1438m, 1346m, 1164m, 1075w, 896w, 815w, 749w, 674w, 547 $cm^{-1}$. $^1H$ n.m.r. spectrum (300 MHz): δ 2.41, s, 2×CH3'; 2.48, s, $CH_3$; 2.50, s, $CH_3$; 2.59, sbr, NH; 6.88–8.07, m, 9H; 10.21, sbr, NH. Mass spectrum: m/z 474 (M+1, 91%), 426 (100), 363 (16), 320 (100), 272 (57), 258 (10), 234 (7), 209 (29), 189 (71), 166 (15), 149 (9), 124 (73), 108 (11).

Example 19 Further compounds according to Table 3

Figure 1:
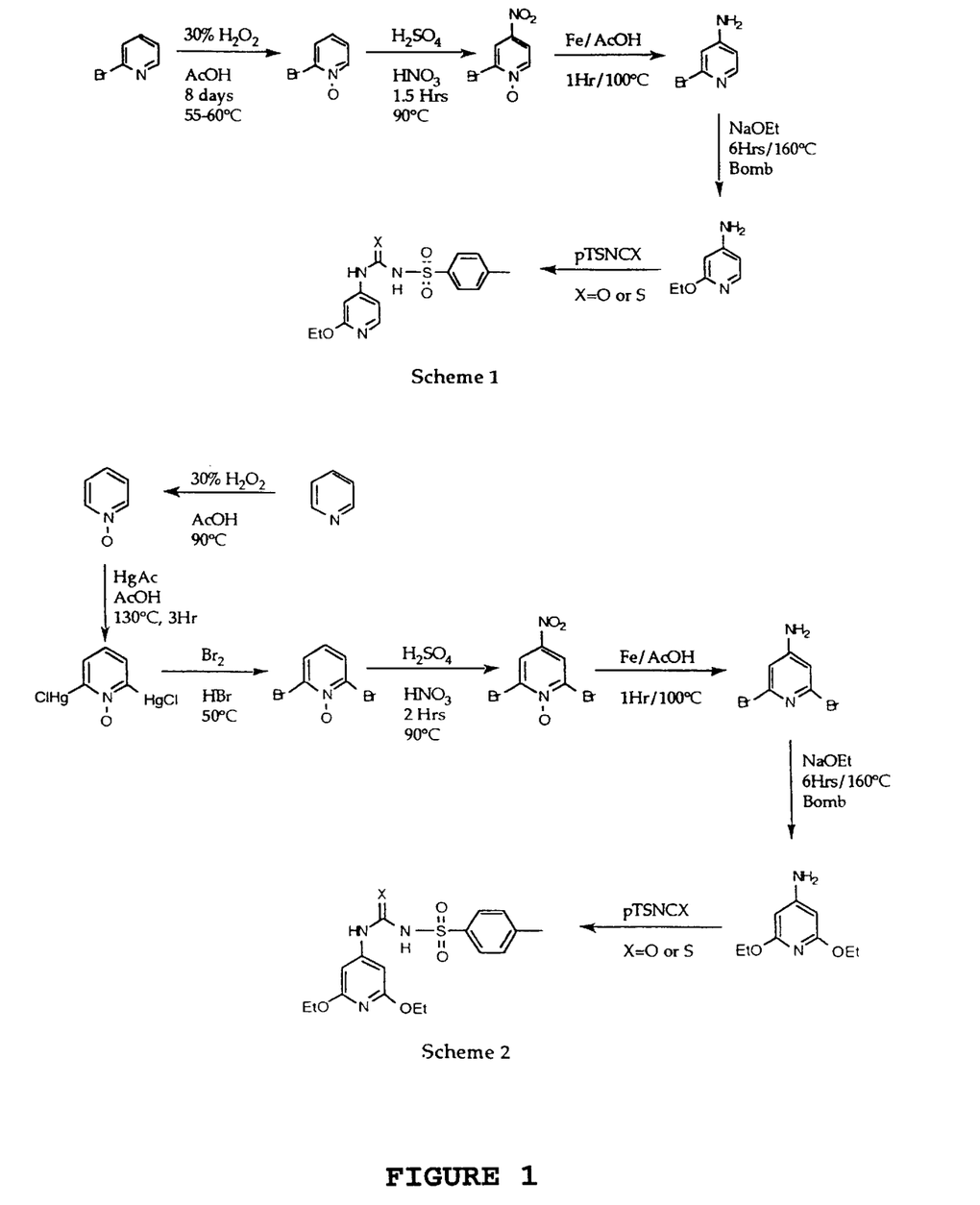
FIG. 1 summarises two synthetic schemes used for preparation of compounds of the invention of the type set out in Table 3 below.
Figure 2:
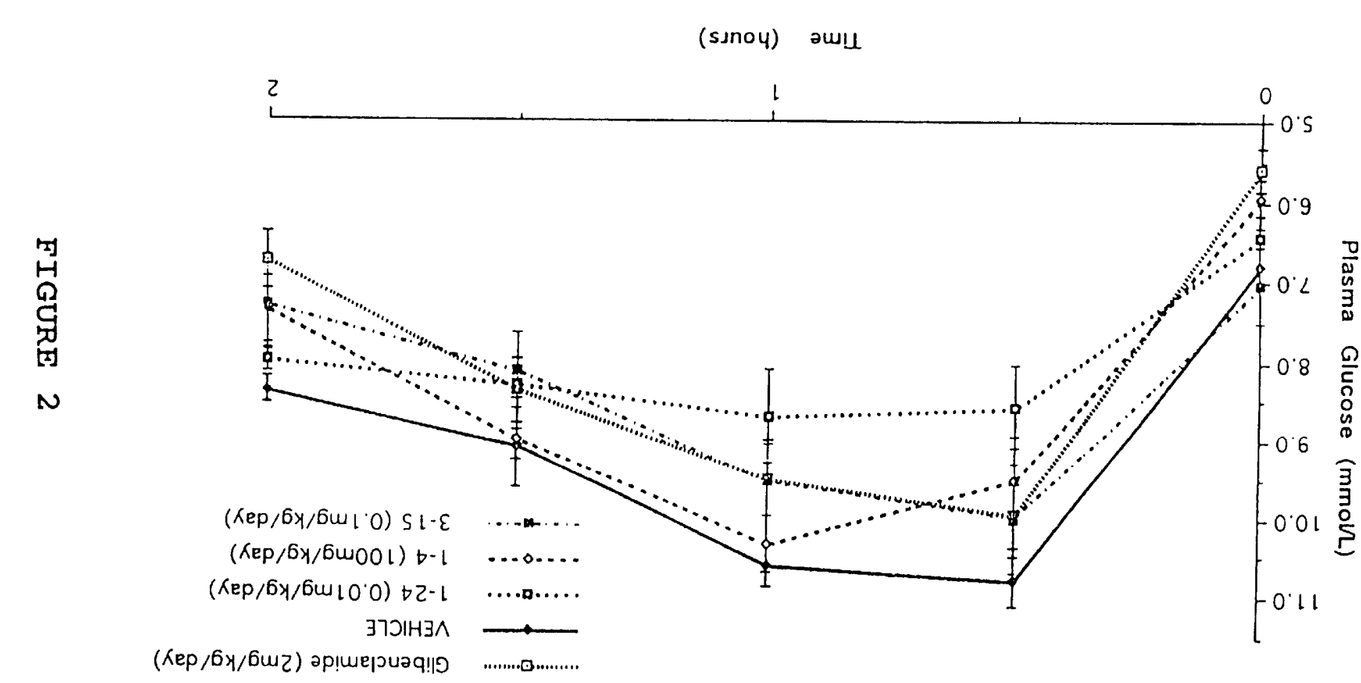
FIG. 2 compares the effect on plasma glucose level of three compounds according to the invention, vehicle alone and Glibenclamide.

Synthesis of Compound 3.23 is described in Example 13. Two general reaction schemes were utilised for preparation of several additional compounds according to Table 3 above. These synthetic schemes are summarised in FIG. 1. Some of the materials used are not readily commercially available, and were prepared according to methods described in the literature, and briefly summarised in Paragraphs a) to f) and i) to l). These starting materials were then used to prepare compounds of the invention, as described in Paragraphs g), h) and m) to o).

a) Pyridine-N-oxide (Den Hertog and Combe, 1951)

Pyridine (70 ml) was mixed with hydrogen peroxide (180 ml) and acetic acid (180 ml). The mixture was stirred at 90° C. overnight, then allowed to cool. The volume was reduced under vacuum, and the solution basified and then extracted with chloroform. The chloroform was then removed under reduced pressure, giving white crystals of pyridine-N-oxide (68 g, 82%).

b) Mercury salt (Van Amers and Den Hertog, 1958)

Pyridine-N-oxide (30 g) was dissolved in acetic acid (250 ml). With stirring, Mercury II acetate was added and the mixture heated to 130° C. for 5 hrs, then allowed to cool. The mixture was then poured into a 10% acetic acid/water solution, and saturated sodium chloride added. The precipitate was filtered, washed, with water and air dried, giving white 2,6-dimercury pyridine-N-oxide.

c) 2,6-dibromopyridine-N-oxide (Van Ammers and Den Hertog, 1958)

The crude mercury salt (40 g) was stirred in water (150 ml) at 50° C. A solution of bromine (10 ml) in saturated sodium bromide (50 ml) was added dropwise and the solution stirred at 50° C. for a further 1.5 hrs. After cooling the solution was basified with sodium hydrogen carbonate and extracted with chloroform. Removal of the chloroform under reduced pressure left a yellow oil of 2,6-dibromopyridine-N-oxide.

d) 4-nitro-2,6-dibromopridine-N-oxide (Van Ammers and Den Hertog, 1958)

2,6-dibromopyridine-N-oxide (6.28 g) was dissolved in concentrated sulphuric acid (20 ml) with stirring. A mixture of concentrated sulphuric acid (20 ml) and concentrated nitric acid (10 ml) was then continuously added dropwise. The solution was then heated at 90° C. for 3 hours with stirring, poured onto ice and then basified with sodium hydroxide. The solution was then continuously extracted with ether, and recrystallised from ethanol to give pale yellow leaflets of 4-nitro-2,6-dibromopyridine-N-oxide (1.2 g, 16%), m.p. 222° C.–224° C.

e) 4-amino-2,6-dibromopyridine (Van Ammers and Den Hertog, 1958)

A mixture of 4-nitro-2,6-dibromopyridine-N-oxide (1.2 g), iron powder (1.2 g) and acetic acid (15 ml) were stirred and heated to 100° C. for 1 hour. Upon cooling the mixture was basified with 3 molar sodium hydroxide and continuously extracted with ether. Removal of the ether under reduced pressure left a white crystalline product of 4-amino-2,6-dibromopyridine (1.0 g, 99%), m.p. 212–214° C.

f) 4-amino-2 6-diethoxypyridine 4-amino-2,6-dibromopyridine (500 mg) was mixed with solid sodium hydroxide (508 mg) and ethanol (15 ml) in a bomb. The bomb was then heated at 160° C. for 6 hrs, allowed to cool, water added and solvent reduced under vacuum. The mixture was then extracted with water and ether. Removal of the ether left an oil of 4-amino-2,6-diethoxypyridine (220 mg, 61%).

g) N-[(4-Methylphenyl)sulphonyl]-N'-(2,6-diethoxypyrid-4-yl)urea (Compound 3-8)

4-amino-2,6-diethoxypyridine (750 mg) was stirred in toluene (15 ml) at 50° C., p-tolueneisocyanate was added dropwise and the mixture stirred for a further 2 hours at 50° C. under nitrogen. The mixture was then stirred for 2 days at room temperature. The precipitate was removed by filtration, and washed with toluene and hot chloroform giving a white crystalline solid of N- [(4-Methylphenyl)sulphonyl]-N'-(2,6-diethoxypyrid-4-yl)urea (838 mg) in quantitative yield, m.p. >270° C. $^1$H n.m.r. spectrum (300 MHz): δ 1.24, t, $J_{CH3}$, 7.90 Hz, 2xCH$_3$, 2.30, s, CH$_3$; 4.08, q, $J_{CH2}$, 7.83 Hz, 2xCH$_2$; 6.46–7.59, m, 3H'; 7.31–7.96, AA'BB', 4H (H3, H5 and H2, H6 respectively).

Mass spectrum: m/z 351 172 (100), 155 (12), 118 (12).

h) N- [(4-Methylphenyl)sulphonyl]-N'-(2,6-dibromopyrid-4-yl)thiourea (Compound 3-24)

4-amino-2,6-dibromopyridine was stirred in toluene (15 ml) at 70°20 C., p-tolueneisothiocyanate was added dropwise and the mixture stirred for a further 8 hours at 70° C. under nitrogen. The mixture was then stirred overnight at room temperature. The precipitate was removed by filtration, washed with toluene and recrystallised from water giving a white crystalline solid of N- [(4-Methylphenyl)sulphonyl]-N'-(2,6-dibromopyrid-4-yl)urea (224 mg) m.p. 124–125° C.

$^1$ n.m.r. spectrum (300 MHz): δ 2.44, s, CH$_3$, 7.26, s, 2H'; 7.34–7.83, AA'BB', 4H (H3, H5 and H2, H6 respectively).

Mass spectrum: m/z 465 (M, <1%), 200 (7), 172 (100), 155 (9).

i) 2-Bromopyridine-N-oxide (Den Hertog, Kolder and Combe, 1951)

2-Bromopyridine (12 g), hydrogen peroxide (30%, 90 ml) and acetic acid (90 ml) were heated at 55–60° C. for 8 days with stirring. The solvent was then reduced under vacuum, water added, and the process repeated 3 or 4 times, to remove all solvent. A greenish oil/solid of 2-Bromopyridine-N-oxide (2.2 g,20%) was obtained.

j) 2-Bromo-4-nitro-pyridine-N-oxide (Den Hertog, Kolder and Combe, 1951)

2-Bromopyridine-N-oxide (28.36 g) was carefully dissolved in concentrated sulphuric acid (43 ml) with stirring. A mixture of concentrated sulphuric acid (65 ml) and concentrated nitric acid (43 ml) was added dropwise, and the mixture refluxed for 3 hours and allowed to cool to room temperature. The mixture was then poured on to ice and the precipitate removed by filtration, washed with water and air dried leaving a fine yellow powder of 2-Bromo-4-nitro-pyridine-N-oxide (14.08 g, 63%), m.p. 145–147° C.

k) 2-Bromo-4-aminopyridine (Den Hertog, Kolder and Combe, 1951)

2-Bromo-4-nitro-pyridine-N-oxide (4 g) was stirred in acetic acid (65 ml) at room temperature and iron powder (4 g) added The mixture was then heated to 100° C. for 1 hour, allowed to cool to room temperature and diluted with water. The mixture was then basified with sodium hydroxide (3M) and continuously extracted with ether, giving a white crystalline solid of 2-Bromo-4-aminopyridine (3.1 g) in quantitative yield, m.p. 97–99° C.

l) 2-Ethoxy-4-aminopyridine (Den Hertog, Kolder and Combe, 1951)

2-Bromo-4-aminopyridine (4 g). solid sodium hydroxide (4 g) and ethanol (15 ml) were heated in a bomb at 160° C. for 6 hours and allowed to cool. Water was then added and the solvent partially removed under reduced pressure. The mixture was then extracted with ether and the solvent removed, leaving a clear oil of 2-Ethoxy-4-aminopyridine (164 g, 76%) which slowly crystallised into colourless needles, m.p. 88–89° C.

m) N- [(4-Methylphenyl)sulphonyl]-N'-(2-ethoxypyrid-4-yl)urea (Compound 3-4)

4-amino-2-ethoxypyridine (518 mg) was stirred in toluene (15 ml) at 50° C., p-tolueneisocyanate was added dropwise and the mixture stirred for a further 2 hours at 50° C. under nitrogen. The mixture was then stirred for 2 days at room temperature. The precipitate was removed by filtration, and washed with toluene and hot chloroform giving a white crystalline solid of N- [(4-Methylphenyl)sulphonyl]-N'-(2-ethoxypyrid-4-yl)urea (1.2 g, 93%), m.p. 146–148° C.

$^1$H n.m.r. spectrum (300 MHz): δ 1.30, t, $J_{CH3}$, 7.77 Hz, CH$_3$; 2.45, s, CH$_3$, 4.29, q, $J_{CH2}$; 7.87 Hz, CH$_2$; 6.95–8.19 m, 3H'; 7.44–7.98 AA'BB', 4H (H3, H5 and H2, H6 respectively).

Mass spectrum: m/z 335 (M+1, 29%), 198 (100), 172 (23), 155 (29), 139 (88), 111 (19).

n) N- [(4-Methylphenyl)sulphonyl]-N'-(2-ethoxypyrid-4-yl)thiourea (Compound 3-15)

4-amino-2-ethoxypyridine (550 mg) was stirred in toluene (15 ml) at 70° C., p-tolueneisothiocyanate was added dropwise and the mixture stirred for a further 8 hours at 70° C. under nitrogen. The mixture was then stirred overnight at room temperature. The precipitate was removed by filtration, and washed with toluene and hot chloroform giving a white crystalline solid of N-[(4-Methylphenyl)sulphonyl]-N'-(2-ethoxypyrid-4-yl)thiourea (1.4 g, 98%), m.p. 152–153° C.

(Found: C,51.3; H, 4.9; N, 11.7. $C_{15}H_{17}N_3O_3S_2$ requires C, 51.3; H, 4.9; N, 12.0%). $^1$H n.m.r. spectrum (300 MHz): δ 1.19, t, $J_{CH3}$, 7.67 Hz, CH$_3$, 2.27, s, CH$_3$; 3.96, q, $J_{CH2}$, 7.47 Hz, CH$_2$; 6.24–7.69, m, 3 H'; 7.23–7.62, AA'BB', 4H (H3, H5 and H2, H6 respectively).

Mass spectrum: m/z 351 (H+1, 90%), 214 (80), 181 (9), 172 (16), 155 (26), 139 (100), 111 (20).

o) N- [(4-Methylphenyl)sulphonyl]-N'-(2-bromopyrid-4-yl)urea (Compound 3-1)

4-amino-2-bromopyridine (200 mg) was stirred in toluene (15 ml) at 50° C., p-tolueneisocyanate was added dropwise and the mixture stirred for a further 2 hours at 50° C. under nitrogen. The mixture was then stirred for 2 days at room temperature. The precipitate was removed by filtration, washed with toluene and hot chloroform giving a white crystalline solid of N- [(4-Methylphenyl)sulphonyl]-N'-(2-bromopyrid-4-yl)urea (140 mg, 36%), m.p. 144–146° C.

(Found: C, 38.6; H, 3.3; N, 10.1; S, 8.0. $C_{13}H_{12}N_3O_3SBr.2H_2O$ requires C, 38.4; H, 3.9; N, 10.3; S, 7.9%). $^1$H n.m.r. spectrum (300 MHz): δ CH$_3$; 2.28, s, CH$_3$. 7.16–7.90, m, 3H'; 7.24–7.66, AA'BB', 4H (H3, H5 and H2, H6 respectively).

Mass spectrum: m/z 370 (M, 14%), 198 (100), 173 (94), 155 (34), 135 (16), 109 (10).

Example 20 Hypoglycaemic Activity of Compounds of the Invention

The biological activity of representative compounds of the invention was evaluated by means of several different tests. The activity of compounds of this invention as hypoglycaemic agents was measured and compared with the activity of the known compound of Example 1, using methods described in the literature. Thus normal, fed male Sprague Dawley rats weighing between 275 and 375 g were studied for changes in blood sugar levels and alterations to mean arterial blood pressure following administration of representative compounds of the invention suspended in a 5% solution of gum acacia by oral gavage at a dose of 1.6 mg/kg. The concentration of each compound was 4 mg in 10 ml, so that each rat received 1.1–1.5 ml to obtain the desired dose on a body weight basis. The blood sugar levels were recorded for each rat immediately prior to administration, and at 1, 2, and 3 hr following administration of the test compounds. Blood glucose levels were determined on blood samples taken from the tail, and analysed on an Ames blood glucometer, model 5626, and Ames, 2627 blood glucose strips (number 2). The results are recorded in Table 6, and show that the compounds of the invention possess substantial hypoglycaemic activity, at least comparable to that of compound of Example 1. These results also show that the onset and the duration of the hypoglycaemic activity are both affected by the specific nature of the heterospecific substitution. It is apparent that generally the heterocyclic sulphonylthioureas have greater activity than the sulphonylureas. Without wishing to be bound by any proposed mechanism for the observed effect, we believe that this may be associated with differences in lipid permeability.

TABLE 6

| Compound No. | Change in Blood Glucose (mmol/L) | | | |
|---|---|---|---|---|
| | 0 hours | 1 Hour | 2 Hours | 3 Hours |
| Compound of Example 1 | 0.0 | −0.8 | −2.1 | −0.8 |
| 1–24 | 0.0 | 0.5 | −2.2 | −1.8 |
| 4–36 | 0.0 | −1.1 | −1.6 | −1.3 |
| 5–38 | 0.0 | −1.7 | −1.4 | −1.2 |
| 1–21 | 0.0 | −0.9 | −2.1 | −0.7 |
| 3–23 | 0.0 | −1.0 | −1.4 | −2.1 |
| Glibenclamide | 0.0 | 0.6 | −2.1 | −2.4 |

Example 21 Effect of Compounds of the Invention on Glucose Tolerance and Weight Gain Representative compounds were evaluated for their effect on glucose tolerance following oral administration at doses ranging from 0.005 mg/kg to 100 mg/kg. Normal male Sprague-Dawley rats were dosed with a test compound daily for five days, and were fasted overnight prior to days 1 and 5. Control animals were given ether vehicle only, or Glibenclamide (glyburide; N-[4-($\beta$-)(2-methoxy-5-chlorobenzamido)ethyl)benzosulphonyl)-N'-cyclohexylurea]; 2 mg/kg/day). Blood was collected on day zero and on days one and five at 0, 0.5, 1, 1.5 and 2 hours after drug administration. Blood glucose concentrations were then measured in duplicate using standard glucose oxidase analysis. The samples were assayed using a Hitachi U-200 Spectrophotometer at a wavelength of 505 nm. The weight gain of each rat was also measured over the five day period, and all results were compared to both the negative control group (dosing with vehicle only) and the positive control group (dosing with Glibenclamide). It was found that at higher doses of drug, including Glibenclamide (the positive control), the rats decreased their observed weight gain over a five day period when compared to rats dosed with vehicle only (negative control). Doses of drugs administered were minimised so as to reduce differences in weight gain whilst retaining hypoglycaemic activity. The results are summarised in FIGS. 3a and 3b, in which the solid line represents weight gain and the dashed line represents glucose tolerance.

Figure 3A:
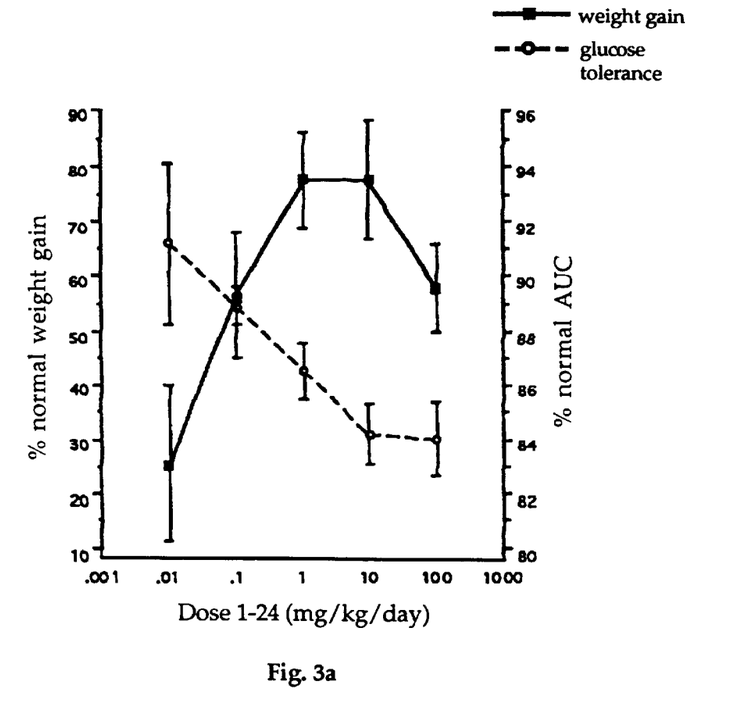
FIGS. 3a and 3b show the relationship between dose, weight gain, and area under the curve for two compounds of the invention. The error bars represent standard error of the mean.
Figure 3B:
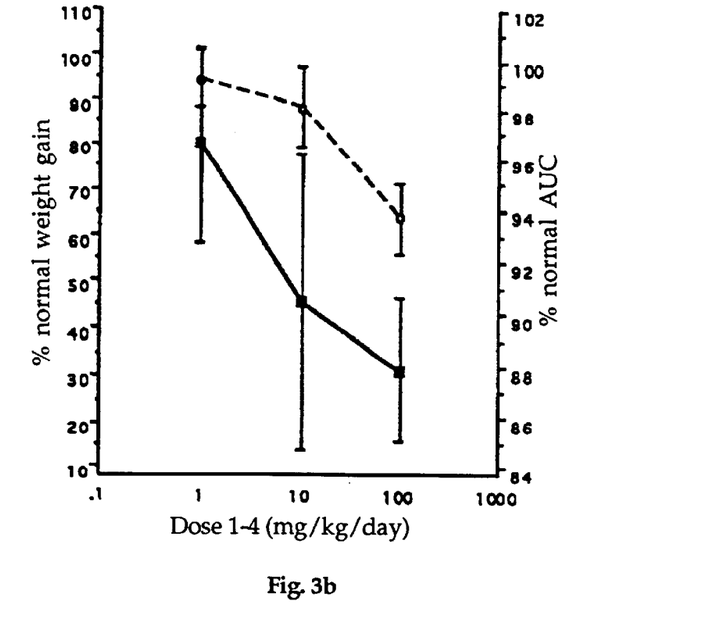

Each point represents the effect of each dose on the rats glucose tolerance or ability to gain weight, expressed as a percentage of the control (normal) response (where control= 100% response). The bars represent standard error.

ie. percentage=weight gain/weight gain (control)×100 and percentage=AUC/AUC (control)×100

Example 22 Cardiac Effects of Compounds of the Invention

Preliminary investigations were performed on isolated atrial preparations, and the results obtained using representative compounds of the invention compared to those obtained using the known compound of Example 1 and using Glibenclamide. English short-haired guinea pigs weighing between 200 and 300 g were killed by cervical dislocation. The whole heart was quickly removed by dissection and immersed in a Krebs-Henseleit solution, which had been aerated with carbogen (95% oxygen and 5% carbon dioxide). The atria were then separated by dissection in Krebs-Henseleit solution, whilst being aerated with carbogen.

The atria were then immersed in a 10 ml organ bath containing Krebs-Henseleit solution, maintained at 37° C. for the duration of the experiment by the circulation of water through the water jackets of organ baths by a temperature controlled water pump (Braun Thermomix, Germany), and aerated with carbogen. The tip of the rounded atrium was pierced by the hook of the muscle holder, while the more pointed tip of the other atrium was tied by a thread connecting the free beating atria to a Grass force—displacement isometric transducer (FT03). Changes in tension were measured by isometric force transducers and were recorded on a four channel Grass 7P Polygraph (Grass Instruments, Quincy, Mass., USA) which was calibrated daily such that the atria functioned with a resting tension of 1 g. The rate of beating of the atria was measured by the tachograph.

Figure 4:
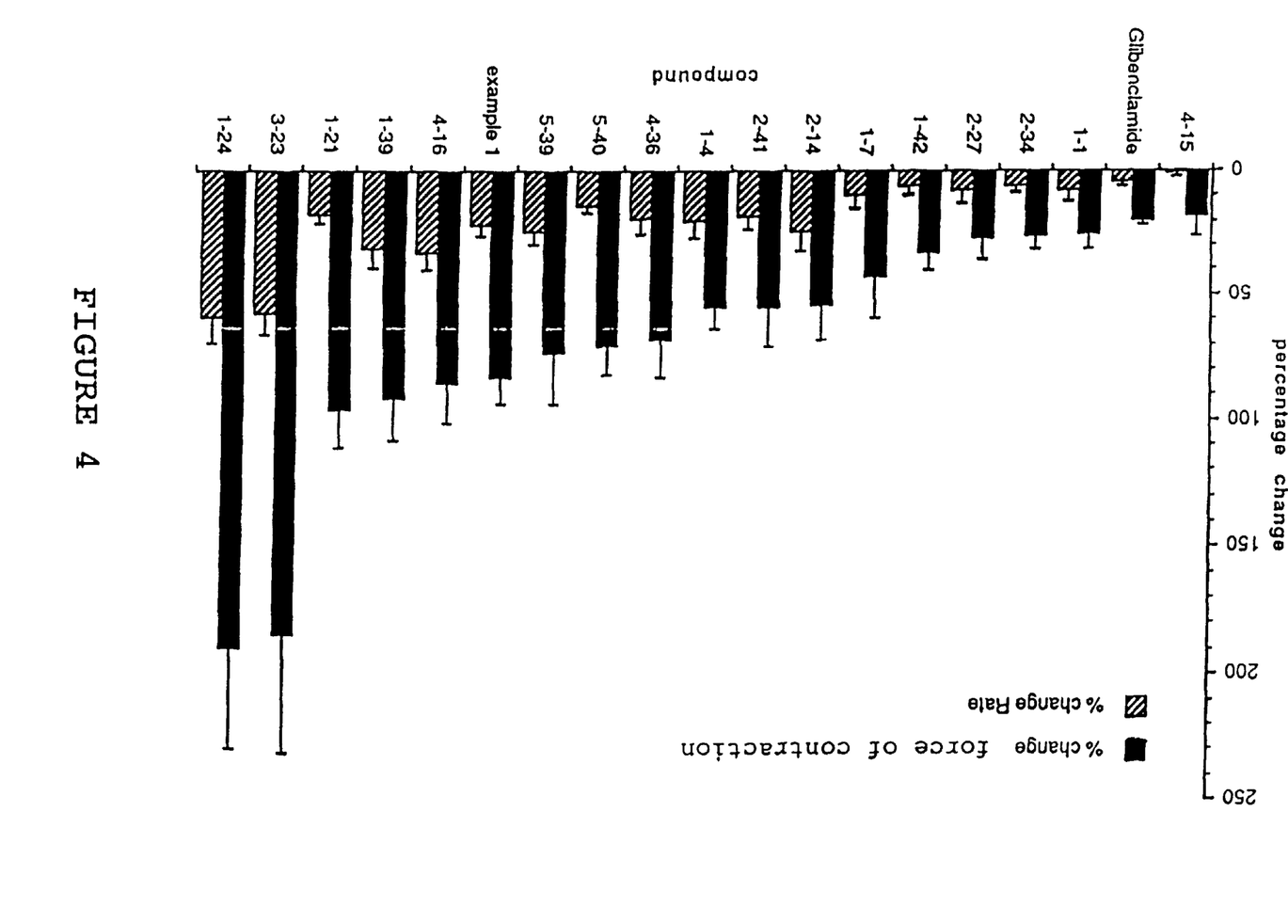
FIG. 4 shows the responses of isolated guinea pig atria to compounds of the invention The error bars represent standard error of the mean.

The activity of each test compound was assessed and compared to that of glibenclamide. A constant single dose of 0.8 ml of a $1\times10^{-4}$ M solution of each of the test compounds and of glibenclamide or of compound of Example 1 was examined such that the bath concentration was $8\times10^{-6}$ M. Maximum responses were recorded and used in analysis. The results are presented in FIG. 4, and demonstrate that most of the test compounds display a comparable or superior response to those obtained with glibenclamide but in most cases have greater inotropic activity. Compounds 1–24 and 3–23 showed particularly marked inotropic activity.

Example 23 Kinetic/Metabolite Studies

Plasma samples were collected in order to test the correlation of plasma drug (or metabolite) concentration with hypoglycaemic activity, and to determine whether compounds of the invention were converted in vivo into active metabolites. The plasma levels of test compounds or metabolites also give an indication of rate of metabolism and kinetics of drug action.

Blood samples collected from rats treated as above and collected at the same intervals were analysed using an ICI LC1150 HPLC system and a LC1210 UV detector at a wavelength of 227 nm. The HPLC system used a Merck LiChroCART 125-4 LiChrosphere 100 RP-18 HPLC and LiChrosphere 100 RP-18 guard columns. The mobile phase consisted of 70% acetonitrile and a 30% aqueous sodium phosphate buffer at pH 7.45 and was prepared using standard HPLC grade reagents and distilled water. To improve the resolution of peaks and separation of the compounds a gradient method was established where changes in the concentration of the required buffers and solvents, and the time at which these changes occur is outlined in Table 7. The volumes are expressed as percentages of the total flow rate, with the flow rate remaining constant at 1.2 ml/hr.

TABLE 7

| Time (minutes) | 38 mM Phosphate Buffer (%) | 70% Acetonitrile (%) |
|---|---|---|
| 0.0 | 63.0 | 37.0 |
| 4.0 | 62.0 | 38.0 |

TABLE 7-continued

| Time (minutes) | 38 mM Phosphate Buffer (%) | 70% Acetonitrile (%) |
|---|---|---|
| 12.0 | 57.0 | 43.0 |
| 14.0 | 63.0 | 37.0 |
| 15.0 | 63.0 | 37.0 |

The data were acquired using the WinChrom Data Management system and were calibrated using stock solutions of the test compounds and Glibenclamide as an internal standard dissolved in 100% methanol Plasma (250 μL) collected from the rats were extracted into methanol (700 μL) and 50 μL of Glibenclamide (25 μg/ml). The mixture was then agitated with a vortex mixer for 15 sec and centrifuged for 10 min. The clear supernatant was then carefully aspirated for HPLC analysis.

The results are outlined in Table 8 and show retention times (minutes) for the compounds and their metabolites as analysed by HPLC after oral administration in Sprague-Dawley rats. The urea compound analysed, Compound 1–4 retained its general structure, and no metabolites were observed in the 4 hour period in which samples were collected. The thiourea Compounds 1–24 and 3–15 however, demonstrated very different metabolism and kinetics, with both the test compounds analysed being metabolised within the first 2 hours after administration resulting in the presence of numerous metabolites in the plasma. Glibenclamide is shown for comparison only, none of the metabolites observed with the test compounds correspond to metabolites of Glibenclamide.

supernatant removed 5 ml of the medium was then added to the pellet of cells and resuspended with a 2 ml pipette.

Approximately 10 μL of medium containing the cells was placed in a Neubauer haemocytometer, and the cells were counted in the 4×1 mm² grid per chamber. Cells were then diluted to contain $60 \times 10^4$ cells to be added to "Corning" 24 well plates (16 mm diameter). Wells respectively containing the control group and 100 μM compound 1–24 were established, and 3 wells/group/day were used to perform the cell growth study.

Each well contained 500 μL of medium or of compound 1–24. Plates were incubated for 24 hours before counting. The medium was aspirated with different pipette tips for the different study groups 100 μL of 0.02% EDTA solution was added to each well and incubated for 5 minutes. 200 μL of trypsin-EDTA was then added, and the cells incubated for a further 5 minutes, aspirated, and placed in 0.5 mL Eppendorf tubes before counting in a haemocytometer.

The results are summarised in Table 9 (n=1, in triplicate), and demonstrate that the representative compound 1–24 reduces MCF-7 tumour cell proliferation, while the proliferation rate of the control group is consistent with the proliferation rate normally observed. The doubling rate observed for the control group is approximately 25% greater than that observed with cells exposed to compound 1–24. This indicates that comopunds of the invention are useful as anti-cancer agents.

TABLE 8

Retention Times (min) of Compounds of the Invention and their Metabolites

| Compound | Compound (Standard) | Compound in plasma | Metabolite A | Metabolite B | Metabolite C | Metabolite D |
|---|---|---|---|---|---|---|
| Glibenclamide | 10.28 | no | 2.27 | 5.77 | 6.68 | — |
| 1-4 | 3.48 | yes | — | — | — | — |
| 1-24 | 6.70 | no | 5.7 | 6.7 | — | — |
| 3-15 | 3.20 | no | 3.03 | 3.73 | 5.7 | 8.57 |

Example 24 Effect of Compounds of the Invention on Cell Proliferation

The ability of a representative compound of the invention to inhibit proliferation of a tumour cell line was examined. MCF-7 human mammary carcinoma cells (Woodfork et al, 1995) were grown in 25 cm² Corning flasks in a 5% $CO_2$ water jacket incubator. The medium used for the culture was RPMI 1640 (ICN) and was supplemented with 10% foetal Bovine serum (Cytosystems).

Cells and medium were examined daily to check for growth and infection. The medium was changed every second day. When cells reached 70–80% confluence, the cells were trypsinized with 0.05% trypsin (1:250, "DIFCO") and 0.02% EDTA.

The flasks were firstly washed with a phosphate buffer to remove residual RPMI 1640 medium, then covered with 2 mL of the trypsin solution and left in the incubator for 3–5 minutes. The cells were then transferred to a conical tube containing 2 mL of medium and 10% foetal bovine serum. The cells were centrifuged at 1000 rpm for 3 minutes and the

TABLE 9

Rate of cell growth in MCF-7 cells

| Day | Control (mean cell number) | Compound 1–24 (mean cell number) |
|---|---|---|
| 0 | 60,000 | 60,000 |
| 1 | 58,000 | 74,000 |
| 2 | 110,000 | 93,000 |
| 3 | 188,000 | 143,000 |
| 6 | 355,000 | 230,000 |

Example 25 Effect of Compounds of the Invention on Thymidine Uptake

Incorporation of [methyl-3H] thymidine into DNA was measured as described by Murphy and Lazarus (1983), using MCF-7 mammary carcinoma cells treated with compound 1–24 (100 μH) and a control group. The growth medium from cells cultured as described in Example 24 was aspirated from the wells, and 1 mL of fresh growth medium containing 1 μCi [3H]-thymidine (Amersham) was added to each well After 4 hours incubation, the medium was aspirated and the monolayers were washed three times with ice cold phosphate buffered saline (ICN). This was followed by three washes with 10% (v/v) ice cold trichloroacetic acid, each of 5 minutes duration. After another three washes with absolute ethanol at room temperature of 5 minutes duration, the monolayer was dried at room temperature for 10 minutes. The monolayer was established after incubation for 12 hours with 0.5 N NaOH and 1% Triton-X 100 (Sigma). An aliquot of the cell lysate was added to 10 ml of Ultima Gold (Packard) and counted using a liquid scintillation counter (Packard model 19006A).

Figure 5:
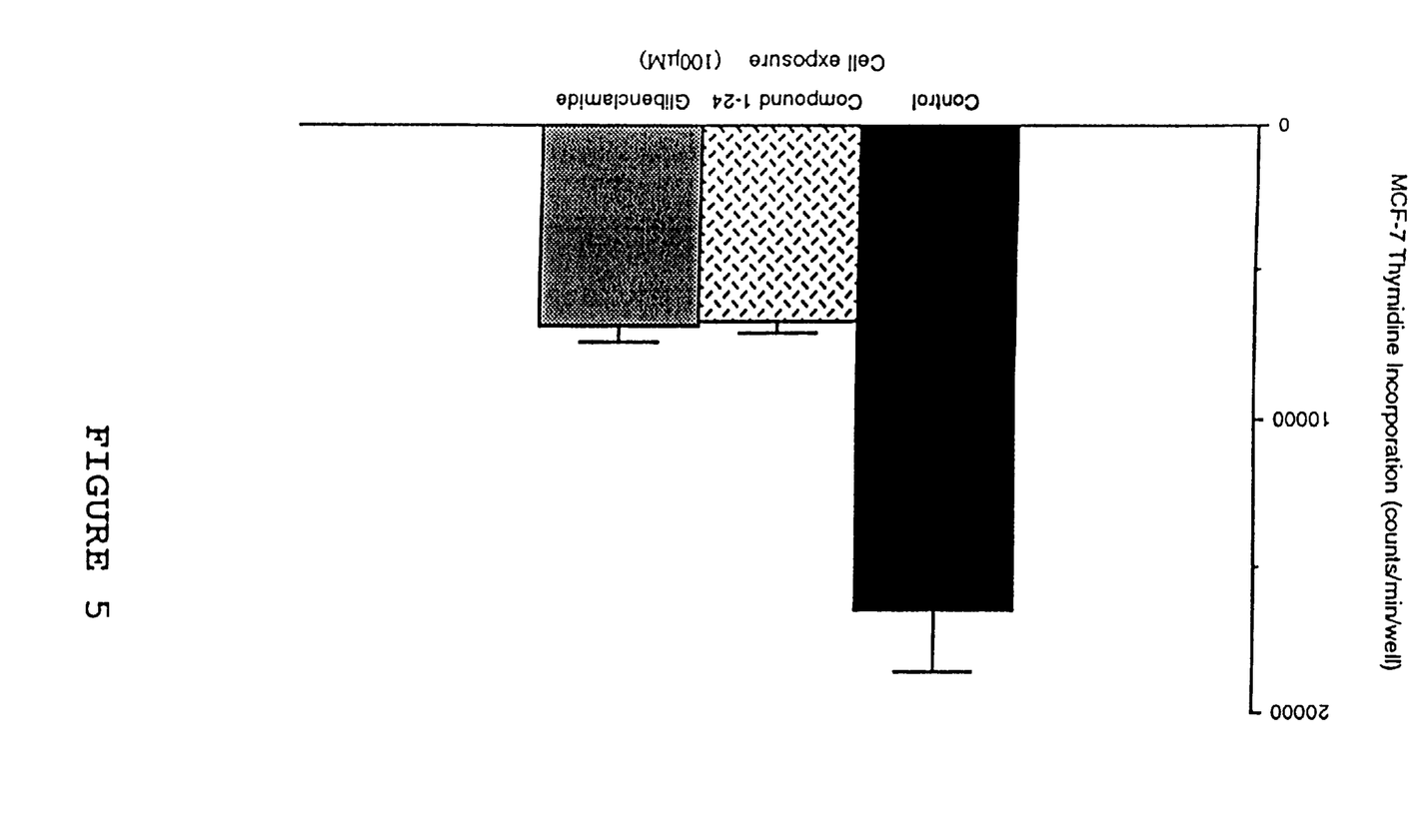
FIG. 5 shows the effect of a compound of the invention on thymidine uptake by MCF-7 tumour cells The error bars represent standard error of the mean.

FIG. 5 shows the inhibition of thymidine uptake in cell populations exposed to 100 mM Glibenclamide (n=3) or Compound 1–24 (n=4), compared to the control group (n=4). The significant inhibition observed supports the inhibition of cell proliferation demonstrated in Example 24, and confirms the potential of compounds of the invention to act as anticancer agents.

Thymidine uptake is a measure of DNA synthesis, which may be either associated with cell proliferation or cell repair Agents which act to inhibit thymidine uptake normally also inhibit cell division, as demonstrated with Compound 1–24.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

1. Cohen, M. L. Drug Development Research, 1986 9 249–258
2. Cook, N. S., Potassium Channels. Structure, Classification, Function and Therapeutic Potential, Ellis Horwood Ltd, Chichester, 1990
3. Den Hertog, H. J. and Combe, W. P. Rec. Trav. Chim., 1951 70 581–590
4. Den Hertog, H. J., Kolder, C. R. and Combe, W. P. Rec. Trav. Chim., 1951 70 591–599
5. Gopalakrishnan, M., Janis, R. A. and Triggle, D. J. Drug Development Research, 1993 28 95–127
6. Kantor, P. F., Coetzee, W. A. Dennis, S. C. and Opie, L. H., Circulation, 76 (Suppl. IV), 1987 17
7. Murphy, L. J. and Lazarus, L. Endocrinology, 1983 112 1026–1035
8. Palmer, K. J. and Brogden, R. N. Drugs, 1993 46 (1) 92–125
9. Robertson, D. W. and Steinberg, N. I. J. Med. Chem., 1990 33 (6) 1529–1541
10. Schmid-Antomarchi, H., Amoroso, S., Fosset, M., and Lazdunski, M. Proc. Natl. Acad. Sci. USA, 1990 87 3489–3492
11. Van Amers, M. and Den Hertog, H. J. Rec. Trav. Chim., 1958 77 340–345
12. Woodfork, K. A., Wonderlin, W. F., Peterson, and Strobl, J. S. Journal of Cellular Physiology, 1995 162 163–171

We claim:

1. A sulphonyl compound of formulae selected from the group consisting of formulae I, II, III, IV and V:

where

R represents a substituted or unsubstituted alkylaryl, benzyl or alkyl group;

X represents oxygen, sulphur, amine, or guanidine;

W represents nitrogen or carbon; and

Y, Q and Z independently represent hydrogen, halogen, amine, alkyl, hydroxy, alkoxy, or sulphonylurea, where each of Y, Q and Z may be the same or different, with the proviso that in formula X, when X is O, Y and Z are not both hydrogen, and in formula IV, X is not O, Y and Z are not $CH_3$, Q is not H, and R is not $C_6H_4CH_3$; and wherein the compound is not or 2. A compound according to claim 1 in which
R represents an alkylaryl group;
X represents oxygen or sulphur;
W represents nitrogen or carbon; and
Y, Q and Z independently represent hydrogen, halogen, amino, alkyl hydroxy, sulphonylurea or alkoxy, where each of Y, Q and Z may be the same or different.

3. A compound according to claim 1 or claim 2 in which one or more of Y, Q and Z is an alkoxy group having 1 to 3 carbon atoms.

4. A compound according to claim 1 in which one or more of Y, Q or Z is a halogen selected from the group consisting of chlorine, bromine or iodine.

5. A compound according to claim 4, wherein one or more of Y, Q and Z is bromine.

6. A compound according to claim 1 in which R is an alkylaryl or benzyl group, and the ring moiety of the R group is substituted with one or more chlorine, bromine, ethyl or methoxy substituents.

7. A compound of formula I, II, III or IV according to claim 1, in which Y, Q or Z is sulphonylurea, and the sulphonylurea group is symmetrical with the sulphonylurea chain which is substituted by the R group.

8. A compound of general formula I, II or III according to claim 1, in which the pyridine ring is substituted by an ethoxy group.

9. A biologically-active metabolite of a compound according to claim 1.

10. A pharmaceutical composition comprising a compound according to claim 1, together with a pharmaceutically-acceptable carrier.

11. A method of treatment of a condition mediated by alteration of potassium ion channel flux, comprising the step of administering an effective amount of a compound according to claim 1 to a mammal in need of such treatment.

12. A method according to claim 11 in which the condition mediated by potassium ion channel flux is selected from the group consisting of type II diabetes, cardiac arrhythmias, ischaemic and hypoxic cardiovascular incidents, and cancers.

13. A process for the preparation of compounds of the formulae I, II, III, IV and V as defined in claim 1 which comprises the step of reacting a compound of the formulae VI, VII, VIII or IX respectively:

wherein W, Y, Z, and Q are as defined above, with a compound of the formula X:

$$X=C=N-\underset{\underset{O}{\|}}{\overset{\overset{O}{\|}}{S}}-R$$

in which X and R are as defined in claim 1.

14. In a method of manufacturing a medicant for the treatment of a condition mediated by alteration of potassium ion channel flux comprising using as the essential ingredient the compound of claim 1.

15. A method according to claim 14 wherein the condition mediated is selected from the group consistent of type II diabetes, cardiac arrhythmias, and ischaemic and hypoxic cardiovascular incidents, and cancers.

* * * * *